(12) United States Patent
Ullberg

(10) Patent No.: US 11,536,860 B2
(45) Date of Patent: Dec. 27, 2022

(54) SENSOR UNIT, RADIATION DETECTOR, METHOD OF MANUFACTURING SENSOR UNIT, AND METHOD USING SENSOR UNIT

(71) Applicant: Direct Conversion AB, Danderyd (SE)

(72) Inventor: Christer Ullberg, Sollentuna (SE)

(73) Assignee: Direct Conversion AB, Danderyd (SE)

( * ) Notice: Subject to any disclaimer, the term of this patent is extended or adjusted under 35 U.S.C. 154(b) by 0 days.

(21) Appl. No.: 17/359,408

(22) Filed: Jun. 25, 2021

(65) Prior Publication Data
US 2021/0405220 A1    Dec. 30, 2021

(51) Int. Cl.
*G01T 1/24* (2006.01)
*A61B 6/03* (2006.01)
*A61B 6/00* (2006.01)

(52) U.S. Cl.
CPC ............ *G01T 1/24* (2013.01); *A61B 6/032* (2013.01); *A61B 6/4241* (2013.01)

(58) Field of Classification Search
CPC .......... G01T 1/24; A61B 6/032; A61B 6/4241
See application file for complete search history.

(56) References Cited

U.S. PATENT DOCUMENTS

| | | | |
|---|---|---|---|
| 5,517,029 | A | 5/1996 | Yanka |
| 9,389,320 | B2 | 7/2016 | Ogawa et al. |
| 2002/0175270 | A1 | 11/2002 | Boemler et al. |
| 2004/0200979 | A1 | 10/2004 | Nam et al. |
| 2005/0247882 | A1 | 11/2005 | Wear et al. |
| 2007/0040100 | A1 | 2/2007 | Zarnowski et al. |
| 2007/0057190 | A1 | 3/2007 | Hatanaka et al. |
| 2010/0252744 | A1* | 10/2010 | Herrmann ............... G01T 1/241 250/370.14 |
| 2011/0121189 | A1 | 5/2011 | Okada |
| 2013/0161525 | A1 | 6/2013 | Okada et al. |
| 2013/0250150 | A1 | 9/2013 | Malone et al. |

(Continued)

FOREIGN PATENT DOCUMENTS

| | | |
|---|---|---|
| EP | 1552683 | 7/2005 |
| EP | 3096513 | 3/2018 |
| JP | 2018048904 | 3/2018 |

OTHER PUBLICATIONS

Swedish Search Report for Application No. 2050777-8 dated Mar. 17, 2021.

(Continued)

*Primary Examiner* — Hugh Maupin
(74) *Attorney, Agent, or Firm* — Laurence & Phillips IP Law

(57) ABSTRACT

Some embodiments include a sensor unit with a conversion element and a readout substrate. The conversion element has imaging pixels and each imaging pixel is configured to directly convert radiation into an electrical charge. Each imaging pixel has a charge collection electrode. The imaging pixels have first imaging pixels and second imaging pixels. The readout substrate has a plurality of readout pixels arranged in a grid. Each readout pixel is connected to an associated imaging pixel by means of an interconnection at a connection position on the charge collection electrode. The second imaging pixels are shifted in a shifting direction relative to the first imaging pixels. The connection positions, in relation to the charge collection electrodes, are different between the first imaging pixels and the second imaging pixels.

21 Claims, 16 Drawing Sheets

(56) References Cited

U.S. PATENT DOCUMENTS

2015/0139390 A1* 5/2015 Bellazzini ................ G01T 1/17
378/62
2019/0179036 A1 6/2019 Takenaka et al.
2019/0348461 A1 11/2019 Yatskan et al.

OTHER PUBLICATIONS

Notification of intention to grant a patent for Application No. 2050777-8 dated Apr. 15, 2021.
EP Application No. 21177811.3, Search Report dated Nov. 16, 2021.

* cited by examiner

SENSOR UNIT, RADIATION DETECTOR, METHOD OF MANUFACTURING SENSOR UNIT, AND METHOD USING SENSOR UNIT

RELATED APPLICATION

The present application claims priority to Swedish Application No. 2050777-8 filed on Jun. 26, 2020, titled "Sensor Unit, Radiation Detector, Method of Manufacturing Sensor Unit, and Method Using Sensor Unit," and assigned to the assignee of the present invention. Swedish Application No. 2050777-8 is incorporated by reference herein.

FIELD OF THE INVENTION

The present disclosure generally relates to a sensor unit. In particular, a sensor unit, a radiation detector comprising a sensor unit, a method of manufacturing a sensor unit for a radiation detector, and a method of using a sensor unit for a radiation detector, are provided.

BACKGROUND

Direct conversion radiation detectors utilize photoconductors, such as a cadmium telluride (CdTe) conversion element, to capture and convert incident X-ray photons directly into electrical charge. The radiation detector may comprise a conversion element having a plurality of imaging pixels and a readout substrate having a plurality of readout pixels. Each readout pixel is typically connected to the center of a charge collection electrode of the associated imaging pixel. Each readout pixel may comprise readout pixel electronics with at least one electronic component specific for an associated readout pixel, such as an amplifier, an integrator, a comparator and/or a counter for counting photon pulses. The space in each readout pixel is typically very limited.

In such photon counting radiation detectors, the resolution is often an important parameter. Increasing the resolution puts high demands on the radiation detector being used, both in terms of small imaging pixels and in terms of small readout pixels. The resolution of some radiation detectors are limited by the size of the readout pixels required to fit the needed electronics in the readout pixels.

In a scanning radiation detector with multiple rows and columns of imaging pixels, the radiation detector can be tilted in the imaging plane so that the same point in an imaged object travels across multiple columns, instead of travelling straight along a single column. By scanning at an angle in this way and sampling with a smaller step (for example sampling every 80 µm for a 100 µm imaging pixel), one can reconstruct an image with higher resolution than the native resolution of the imaging pixels.

SUMMARY

One object of the present disclosure is to provide an improved sensor unit for a radiation detector.

A further object of the present disclosure is to provide a sensor unit for a radiation detector, which sensor unit enables high resolution imaging.

A still further object of the present disclosure is to provide a sensor unit for a radiation detector, which sensor unit has a less complex design for high resolution imaging.

A still further object of the present disclosure is to provide a sensor unit for a radiation detector which sensor unit has a compact design.

A still further object of the present disclosure is to provide a sensor unit for a radiation detector, which sensor unit enables high resolution imaging without needing to tilt the sensor unit in an imaging plane.

A still further object of the present disclosure is to provide a sensor unit for a radiation detector, which sensor unit has an improved modular design.

A still further object of the present disclosure is to provide a sensor unit for a radiation detector, which sensor unit solves several or all of the foregoing objects in combination. In particular, one object is to provide a sensor unit for a radiation detector, which sensor unit both enables high resolution imaging and has a regular grid design of the readout pixels.

A still further object of the present disclosure is to provide a radiation detector comprising a sensor unit, which radiation detector solves one, several or all of the foregoing objects.

A still further object of the present disclosure is to provide a method of manufacturing a sensor unit for a radiation detector, which method solves one, several or all of the foregoing objects.

A still further object of the present disclosure is to provide a method of using a sensor unit for a radiation detector, which method solves one, several or all of the foregoing objects.

According to one aspect, there is provided a sensor unit for a radiation detector, the sensor unit comprising a conversion element comprising a plurality of imaging pixels, each imaging pixel being configured to directly convert radiation into an electrical charge, each imaging pixel comprising a charge collection electrode, and the imaging pixels comprising first imaging pixels and second imaging pixels; and a readout substrate comprising a plurality of readout pixels arranged in a grid, each readout pixel being connected to an associated imaging pixel by means of an interconnection at a connection position on the charge collection electrode; wherein the second imaging pixels are shifted in a shifting direction relative to the first imaging pixels; and wherein the connection positions in relation to the charge collection electrodes are different between the first imaging pixels and the second imaging pixels.

According to a further aspect, there is provided a radiation detector comprising at least one sensor unit according to the present disclosure.

According to a further aspect, there is provided a method of manufacturing a sensor unit for a radiation detector, the method comprising providing a conversion element comprising a plurality of imaging pixels, each imaging pixel being configured to directly convert radiation into an electrical charge, each imaging pixel comprising a charge collection electrode, and the imaging pixels comprising first imaging pixels and second imaging pixels; providing a readout substrate comprising a plurality of readout pixels arranged in a grid; and connecting each readout pixel to an associated imaging pixel by means of an interconnection at a connection position on the charge collection electrode; wherein the second imaging pixels are shifted in a shifting direction relative to the first imaging pixels; and wherein the connection positions in relation to the charge collection electrodes are different between the first imaging pixels and the second imaging pixels.

According to a further aspect, there is provided a method of using a sensor unit for a radiation detector, the method comprising providing a sensor unit comprising a conversion element comprising a plurality of imaging pixels, each imaging pixel being configured to directly convert radiation into an electrical charge, each imaging pixel comprising a charge collection electrode, and the imaging pixels comprising first imaging pixels and second imaging pixels; and a readout substrate comprising a plurality of readout pixels arranged in a grid, each readout pixel being connected to an associated imaging pixel by means of an interconnection at a connection position on the charge collection electrode; wherein the second imaging pixels are shifted in a shifting direction relative to the first imaging pixels; and wherein the connection positions in relation to the charge collection electrodes are different between the first imaging pixels and the second imaging pixels. The method further comprises moving the sensor unit in a scanning direction substantially perpendicular to the shifting direction; generating electric signals responsive to radiation onto the imaging pixels; and sampling the electric signals at successive increments of movement of the sensor unit in the scanning direction equal to or less than a length of each imaging pixel in the scanning direction.

DETAILED DESCRIPTION

Figure 1:
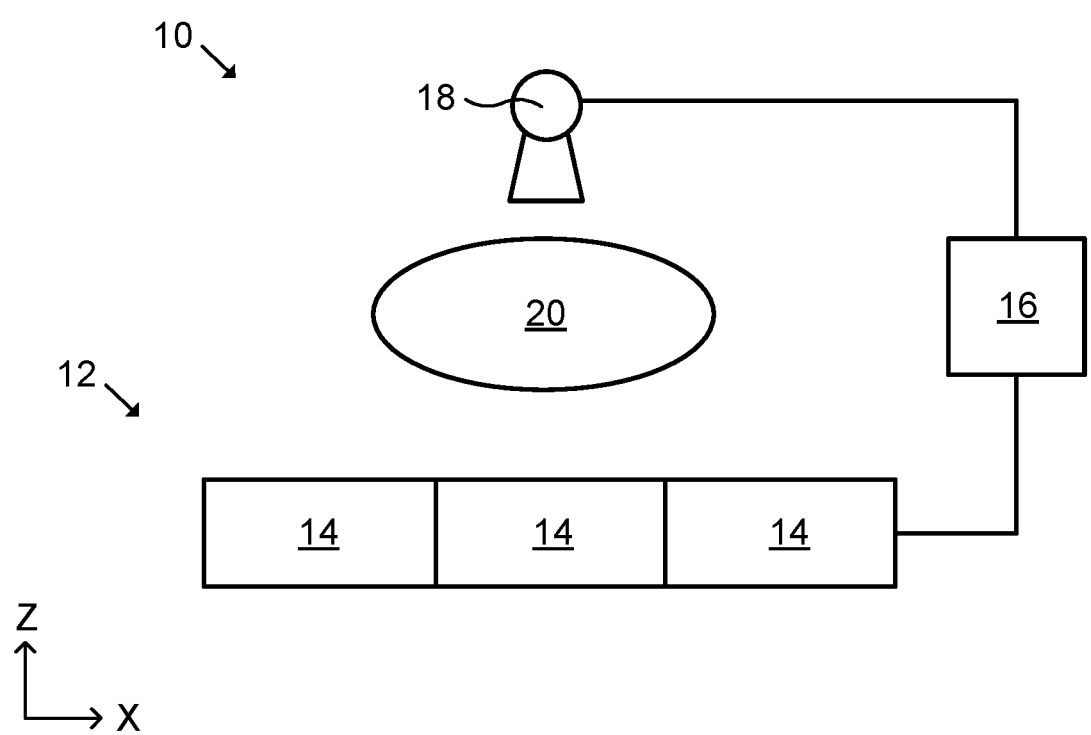
FIG. 1 schematically represents a side view of an imaging apparatus comprising a radiation detector.

In the following, a sensor unit, a radiation detector comprising a sensor unit, a method of manufacturing a sensor unit for a radiation detector, and a method of using a sensor unit for a radiation detector, will be described. The same or similar reference numerals will be used to denote the same or similar structural features.

FIG. 1 schematically represents a side view of an imaging apparatus 10 comprising a radiation detector 12. The radiation detector 12 is a direct conversion scanning radiation detector. The radiation detector 12 of this example is formed of a plurality of sensor units 14 according to the present disclosure. The radiation detector 12 may for example comprise one or more coupling mechanisms that allow for connecting the sensor units 14 together. The coupling mechanisms may for example connect support substrates of two adjoining sensor units 14. The sensor units 14 may also be connected via interface circuits.

A radiation detector 12 according to the present disclosure may however alternatively comprise only one sensor unit 14. The imaging apparatus 10 may for example be a computed tomography (CT) device.

The imaging apparatus 10 comprises a control system 16 and a radiation source 18, such as an X-ray tube, for emitting X-rays that are transmitted through an object 20 to be imaged, for example through the body of a patient. After transmission through the object 20, the X-rays reach the radiation detector 12 where the X-rays are detected and converted into signals representing a spatially resolved projection image of the object 20. The control system 16 may be configured to acquire 2D projection images. The acquired 2D images may be used to reconstruct, for example 3D images, of the object 20 according to known principles of computed tomography.

FIG. 1 further shows two Cartesian coordinates X and Z of a three-dimensional Cartesian coordinate system X, Y, Z for referencing purposes. The radiation detector 12 of this example is planar and oriented in the XY-plane. Thus, an imaging plane of the radiation detector 12 is parallel with the XY-plane. The imaging apparatus 10 and the radiation detector 12 may however be oriented arbitrarily in space.

Figure 2:
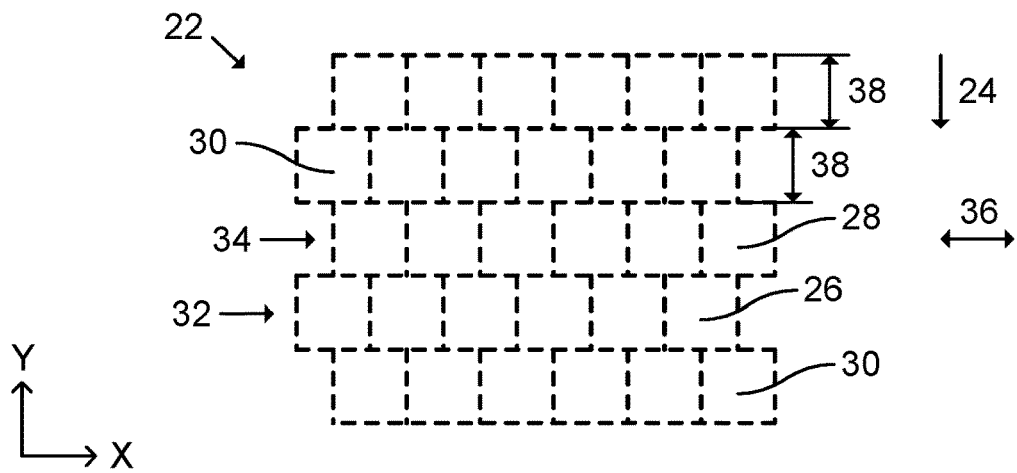
FIG. 2 schematically represents a top view of a conversion element.

FIG. 2 schematically represents a top view of a conversion element 22 of one of the sensor units 14. A scanning direction 24 of the sensor unit 14 is shown in FIG. 2. The conversion element 22 may for example include a CdTe crystal.

The conversion element 22 comprises a plurality of imaging pixels 26, 28. In an example, the imaging pixels 26, 28 are the smallest addressable photo conducting picture element. The imaging pixels 26, 28 can include at least a portion of the conversion element 22 and a charge collection electrode 30. In this example, the imaging pixels comprise first imaging pixels 26 and second imaging pixels 28. Each imaging pixel 26, 28 comprises a charge collection electrode 30. Each imaging pixel 26, 28 is configured to directly convert ionizing radiation into an electrical charge. The imaging pixels 26, 28 are evenly distributed over at least a major part of the sensor unit 14, such as over the entire sensor unit 14.

In this example, each imaging pixel 26, 28 and its associated charge collection electrode 30 has a square shape. The first imaging pixels 26 and the second imaging pixels 28 can have the same or similar size. Also the associated charge collection electrodes 30 can have the same or similar size.

The first imaging pixels 26 and the second imaging pixels 28 can be arranged in rows or columns. In FIG. 2, the first imaging pixels 26 are arranged in first rows 32 and the second imaging pixels 28 are arranged in second rows 34. The first rows 32 and the second rows 34 are alternatingly arranged. As shown in FIG. 2, the second imaging pixels 28 are shifted relative to the first imaging pixels 26 in a shifting direction 36. Each second imaging pixel 28 of a second row 34 is thereby offset with respect to at least one neighboring first imaging pixel 26 of a first row 32. In FIG. 2, each second imaging pixel 28 is shifted to the right in the shifting direction 36.

The second imaging pixels 28 are shifted half a width of the imaging pixels 26, 28 from a position where the second imaging pixels 28 are aligned with the first imaging pixels 26. The shifting direction 36 (in the X-direction) is perpendicular to the scanning direction 24 (in the Y-direction). Both the shifting direction 36 and the scanning direction 24 are thus provided in the imaging plane of the radiation detector 12. Each of the first rows 32 and the second rows 34 is parallel with the shifting direction 36.

Each imaging pixel 26, 28 has a length 38. Each length 38 extends perpendicular to the shifting direction 36 and parallel with the scanning direction 24.

Figure 3:
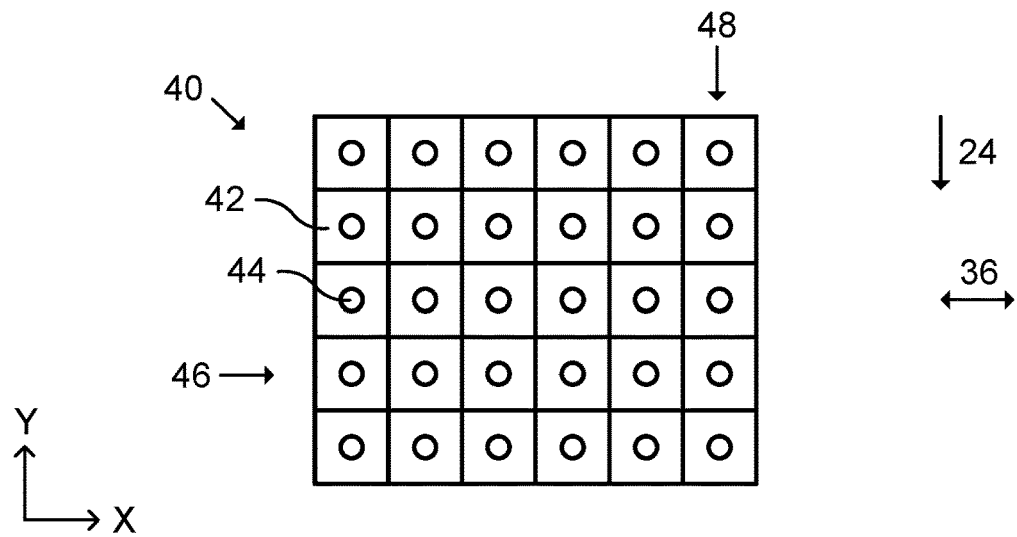
FIG. 3 schematically represents a top view of a readout substrate.

FIG. 3 schematically represents a top view of a readout substrate 40 of the same sensor unit 14 comprising the conversion element 22. The readout substrate 40 may for example be a readout ASIC substrate. The readout substrate 40 may comprise a silicon substrate or a substrate of other suitable semiconductor or insulator.

The readout substrate 40 comprises a plurality of readout pixels 42. Each readout pixel 42 comprises an interconnection 44. The interconnection 44 is arranged to provide an electric connection between the readout pixel 42 and an imaging pixel 26, 28. The interconnection 44 may alternatively be said to be comprised by the imaging pixels 26, 28.

In this example, each readout pixel 42 has a square shape. The readout pixels 42 can have the same or similar size. In an example, the size of the readout pixels 42 substantially matches, or is slightly smaller than, the size of the imaging pixels 26, 28. Size (or area) of the readout pixels 42 and size (or area) of the imaging pixels 26, 28 can have the same or similar sizes (or areas) in planes parallel with the imaging plane. The size of the readout pixels 42 may be said to substantially match the size of the imaging pixels 26, 28 if the size of each readout pixel 42 differs less than 5%, such as less than 2%, from the size of the imaging pixels 26, 28.

The readout pixels 42 are arranged in a grid. In this example, the readout pixels 42 are arranged in a matrix comprising a plurality of readout rows 46 and a plurality of readout columns 48. The readout rows 46 are perpendicular to the readout columns 48. The readout rows 46 are parallel with the shifting direction 36.

In the example in FIG. 3, each interconnection 44 is centered on the associated readout pixel 42, i.e. both in the X-direction and in the Y-direction. Thus, also the interconnections 44 are arranged in a matrix. The distances between the interconnections 44 are even both in the X-direction and in the Y-direction. Thus, none of the readout pixels 42 are shifted. The readout substrate 40 therefore has a regular matrix design (both along the rows and columns). The design of the readout substrate 40 can be used with alternative conversion elements having non-shifted imaging pixels arranged in a regular matrix. This improves modularity of the sensor unit 14.

Figure 4:
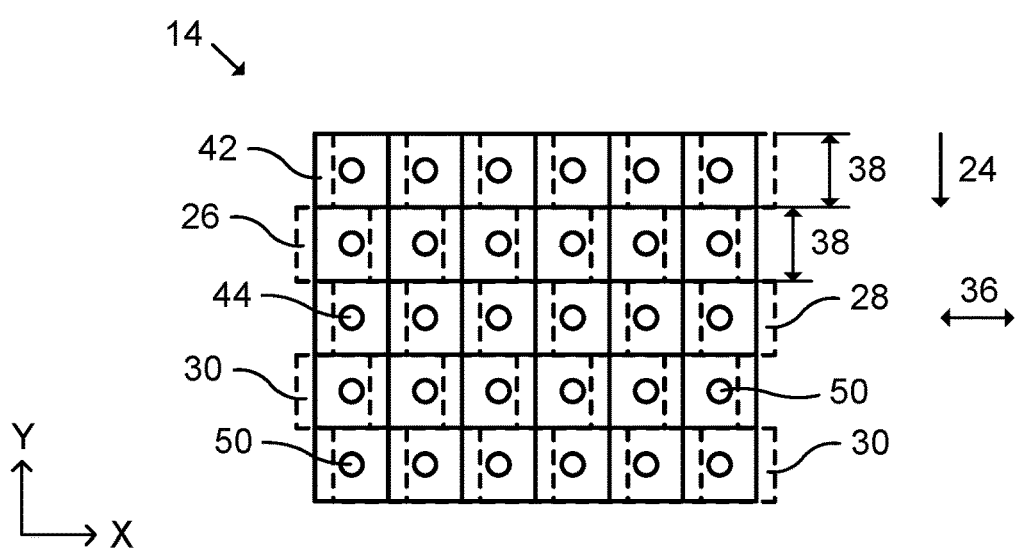
FIG. 4 schematically represents a top view of a sensor unit.

FIG. 4 schematically represents a top view of the same sensor unit 14 comprising the conversion element 22 in FIG. 2 and the readout substrate 40 in FIG. 3. As shown in FIG. 4, each readout pixel 42 is connected to a unique associated imaging pixel 26, 28 by means of a respective interconnection 44 at a connection position 50 on the charge collection electrodes 30. Each first row 32 of first imaging pixels 26 and each second row 34 of second imaging pixels 28 is aligned with a unique readout row 46 of readout pixels 42.

As shown in FIG. 4, the connection positions 50 for the first imaging pixels 26 are on right (in FIG. 4) halves of the associated charge collection electrodes 30, and the connection positions 50 for the second imaging pixels 28 are on the left halves of the associated charge collection electrodes 30. Thus, the connection positions 50 of all imaging pixels 26, 28 are offset with respect to the associated charge collection electrodes 30 in this example. However, the offsets are different between the first imaging pixels 26 and the second imaging pixels 28.

The connection positions 50 in relation to the charge collection electrodes 30 are the same for all first imaging pixels 26, and the connection positions 50 in relation to the charge collection electrodes 30 are the same for all second imaging pixels 28. During scanning of the object 20, the sampling frequency of the radiation detector 12 may be set such that at least one point per row of imaging pixels 26, 28 is obtained.

Figure 5:
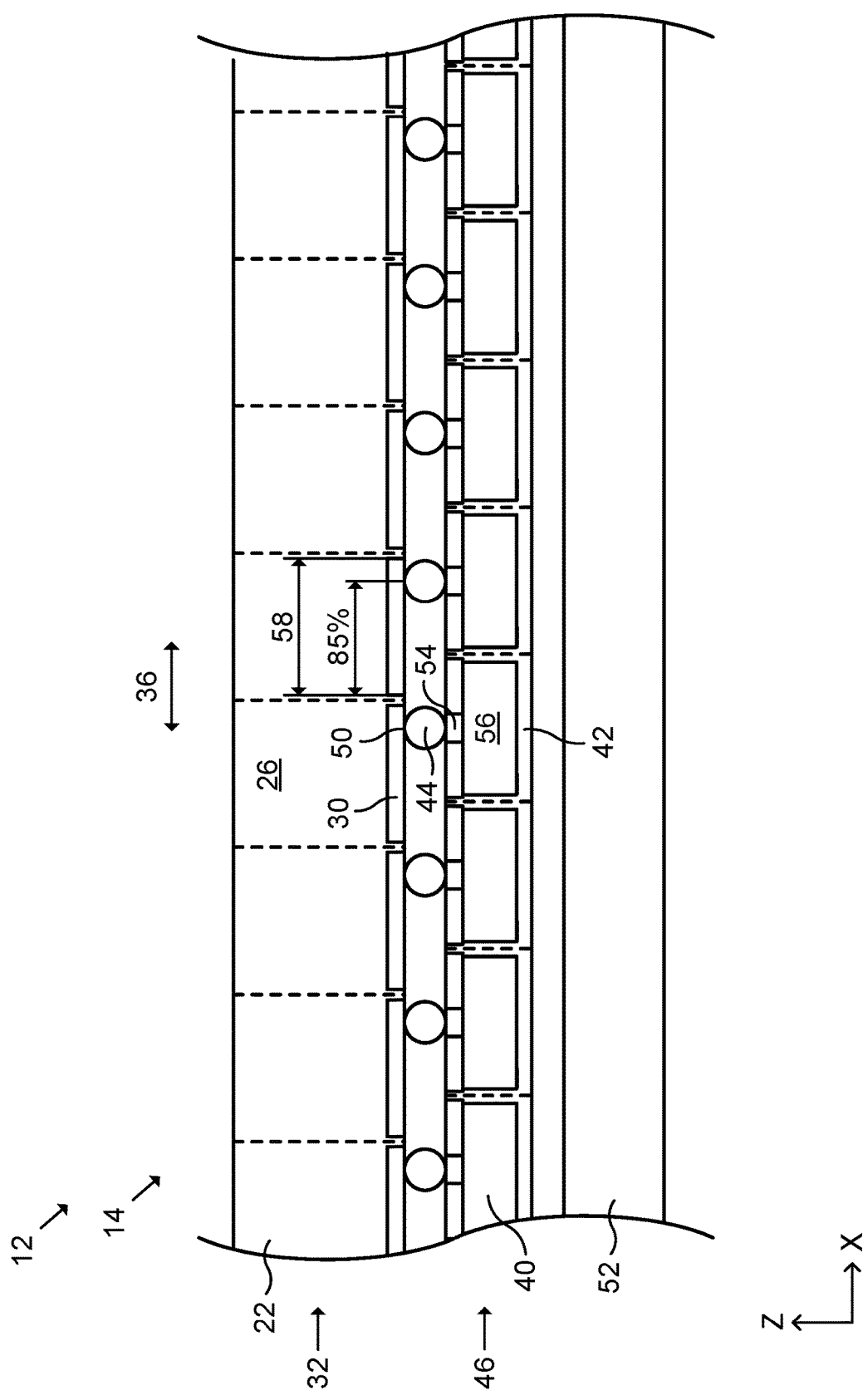
FIG. 5 schematically represents a cross-sectional side view of the sensor unit.
Figure 6:
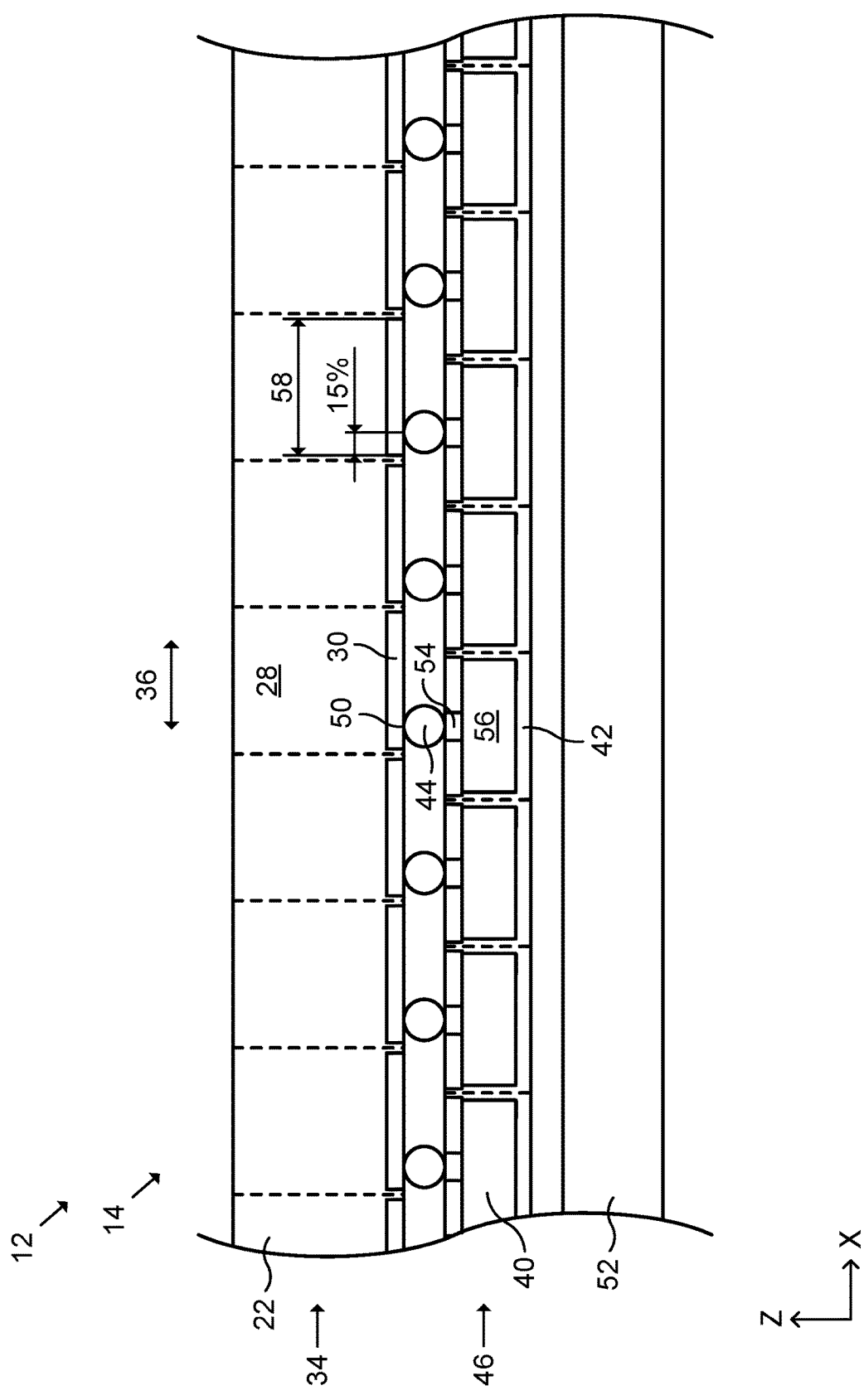
FIG. 6 schematically represents a further cross-sectional side view of the sensor unit.

FIG. 5 schematically represents a cross-sectional side view of the sensor unit 14. The cross-section in FIG. 5 shows the first imaging pixels 26. FIG. 6 schematically represents a further cross-sectional side view of the sensor unit 14. The cross-section in FIG. 6 shows the second imaging pixels 28. With collective reference to FIGS. 5 and 6, the sensor unit 14 comprises, in addition to the conversion element 22 and the readout substrate 40, a support substrate 52. The support substrate 52 may comprise a printed circuit board (PCB), for example of ceramic or glass.

As shown in FIGS. 5 and 6, the charge collection electrodes 30 of the conversion element 22 are here implemented as contact pads embedded in the conversion element 22. The charge collection electrodes 30 define the imaging pixels 26, 28. The charge collection electrodes 30 are separated from each other such that boundaries between adjacent imaging pixels 26, 28 are formed.

When X-rays (or other type of ionizing radiation) impinges on the conversion element 22, electron-hole pairs are created inside the conversion element 22 (hence the term "direct conversion") in response to the absorbed energy. Under the influence of an electrical field applied across the conversion element 22, these electrons (holes) are transferred to associated charge collection electrodes 30.

Each readout pixel 42 comprises a readout electrode 54. The readout electrodes 54 are here exemplified as contact pads. Each pair of one imaging pixel 26, 28 and one readout pixel 42 is connected by means of an interconnection 44. In FIGS. 5 and 6, the interconnections 44 are exemplified as solder bumps between the charge collection electrodes 30 and the associated readout electrodes 54. Each readout electrode 54 thereby acts as the input to the associated readout pixel 42. Each readout electrode 54 receives, through an interconnection 44, an electrical signal generated in the conversion element 22 by the absorption of an X-ray photon. The conversion element 22 and the readout substrate 40 may be connected by means of flip-chip bonding, or by any other means of forming electrical contact.

Each readout pixel 42 comprises readout pixel electronics 56 dedicated to the readout pixel 42. Thus, the readout pixel electronics 56 comprise at least one electronic component with a function specific for the associated readout pixel 42. The readout pixel electronics 56 of the readout pixels 42 may for example be suitable for processing or interpreting signals generated by the X-ray photons incident on the conversion element 22. Non-limiting examples of readout pixel electronics 56 include a filter, an amplifier, an integrator, a comparator and/or a counter for counting photon pulses. According to one example, each readout pixel 42 comprises a preamplifier and a comparator for sensing pulse size.

In one example, the combined area (in the XY-plane) of the readout pixel electronics 56 and associated features defines the area of the readout pixel 42. An outer edge (in the XY-plane) of a readout pixel electronic feature to another outer edge of another readout pixel electronic feature on an opposite side of the readout pixel 42 can define a boundary of the readout pixel 42. A readout pixel first width in the first direction extends over a maximum distance between two readout pixel boundaries in the X-direction. A readout pixel second width in the second direction extends over a maximum distance between two readout pixel boundaries in the Y-direction.

Providing offsets between the readout pixels 42 can be more difficult and complicate a complementary metal-oxide-semiconductor (CMOS) ASIC design relative to a regular grid, such as a matrix. Offsetting the imaging pixels 26, 28 instead and coupling them to the readout pixels 42 in a regular matrix configuration can simplify the design. Even though the imaging pixels 26, 28 are offset from the readout pixels 42, the charge collection electrodes 30 are good electric conductors, and the electric field will be straight and direct the electrical charge to the correct readout pixel 42 regardless of the connection position 50 on the charge collection electrode 30. This enables the connection positions 50 on the first imaging pixels 26 and the second imaging pixels 28 to be different in relation to the respective charge collection electrodes 30 while the readout pixels 42 are arranged in a regular matrix in the readout substrate 40.

As shown in FIG. 5, the connection positions 50 of the first imaging pixels 26 in relation to the charge collection electrodes 30, expressed in a percentage of a width 58 of the respective charge collection electrode 30 in the shifting direction 36 from left to right, is approximately 85%. As shown in FIG. 6, the connection positions 50 of the second imaging pixels 28 in relation to the charge collection electrodes 30, expressed in a percentage of a width 58 of the respective charge collection electrode 30 in the shifting direction 36 from left to right, is approximately 15%. Thus, the connection positions 50 in relation to the charge collection electrodes 30 of the first imaging pixels 26 and the second imaging pixels 28, expressed in a percentage of the width 58 of the respective charge collection electrode 30 in the shifting direction 36, differs by 70% between the first imaging pixels 26 and the second imaging pixels 28.

A distance between an edge of the charge collection electrode 30 and an associated connection position 50 may be as small as 5 μm, or less. A connection position 50 may also be provided right on the edge of an associated charge collection electrode 30.

By shifting the second imaging pixels 28 in the shifting direction 36 relative to the first imaging pixels 26 and using different connection positions 50 on the charge collection electrodes 30 for the first imaging pixels 26 and the second imaging pixels 28, the image resolution can be increased without having to tilt the sensor unit 14 and without having to provide corresponding shifts to any of the readout pixels 42.

Figure 7:
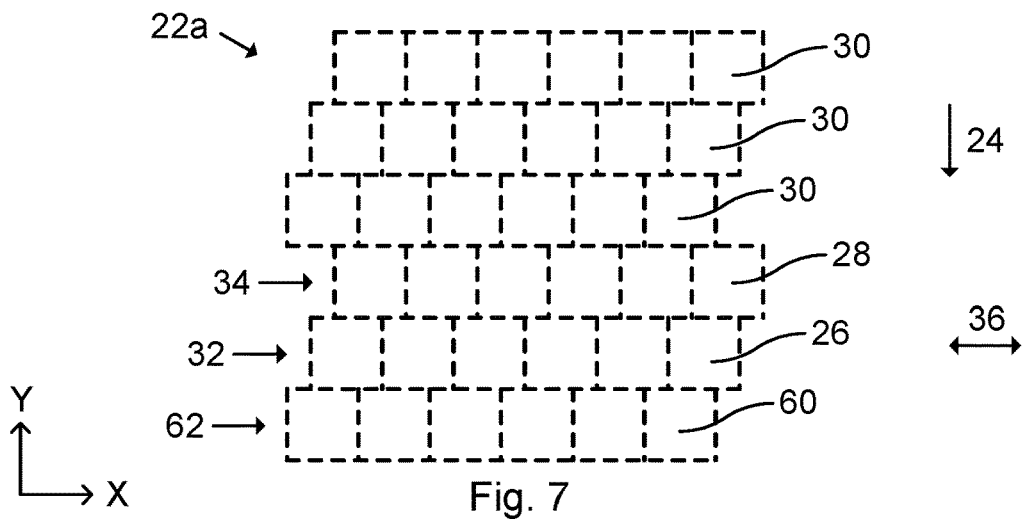
FIG. 7 schematically represents a top view of a further conversion element.

FIG. 7 schematically represents a top view of a further conversion element 22a. Mainly differences with respect to FIGS. 2 to 6 will be described. The conversion element 22a in FIG. 7 comprises a plurality of imaging pixels constituted by first imaging pixels 26, second imaging pixels 28 and third imaging pixels 60.

The first imaging pixels 26 are arranged in first rows 32. The second imaging pixels 28 are arranged in second rows 34. The third imaging pixels 60 are arranged in third rows 62. The first rows 32, the second rows 34 and the third rows 62 are alternatingly arranged and parallel with the shifting direction 36.

The second imaging pixels 28 are shifted relative to the first imaging pixels 26 in the shifting direction 36 to the right. The third imaging pixels 60 are shifted relative to the first imaging pixels 26 in the shifting direction 36 to the left. The second imaging pixels 28 are shifted to the right a third of a width of the imaging pixels 26, 28, 60 from a position where the second imaging pixels 28 are aligned with the first imaging pixels 26. The third imaging pixels 60 are shifted to the left a third of a width of the imaging pixels 26, 28, 60 from a position where the third imaging pixels 60 are aligned with the first imaging pixels 26.

Figure 8:
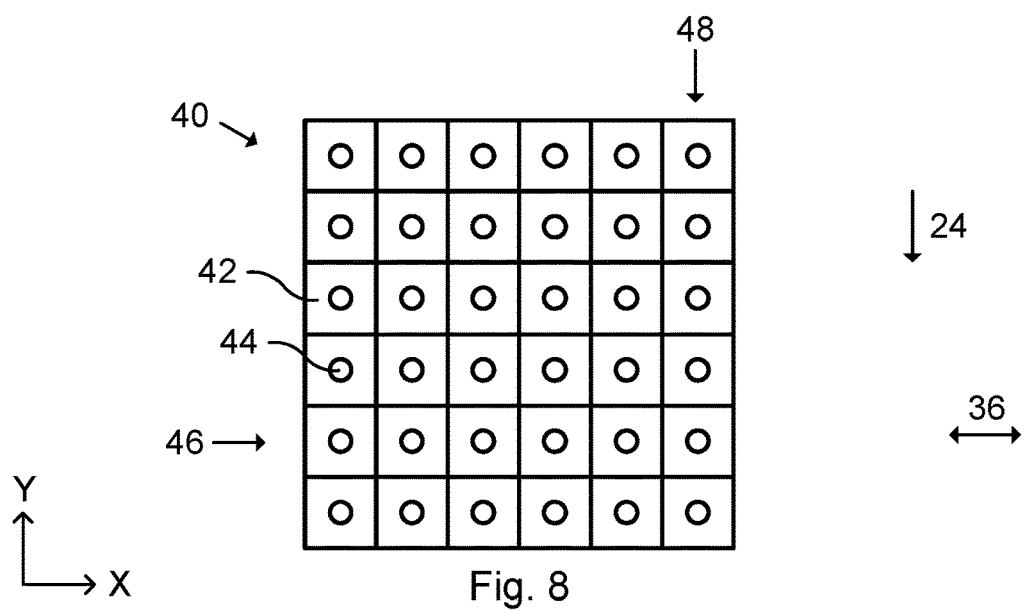
FIG. 8 schematically represents a top view of a readout substrate.

FIG. 8 schematically represents a top view of a readout substrate 40. The readout substrate 40 in FIG. 8 is of the same type as in FIG. 4 (although one more readout row 46 is shown in FIG. 8).

Figure 9:
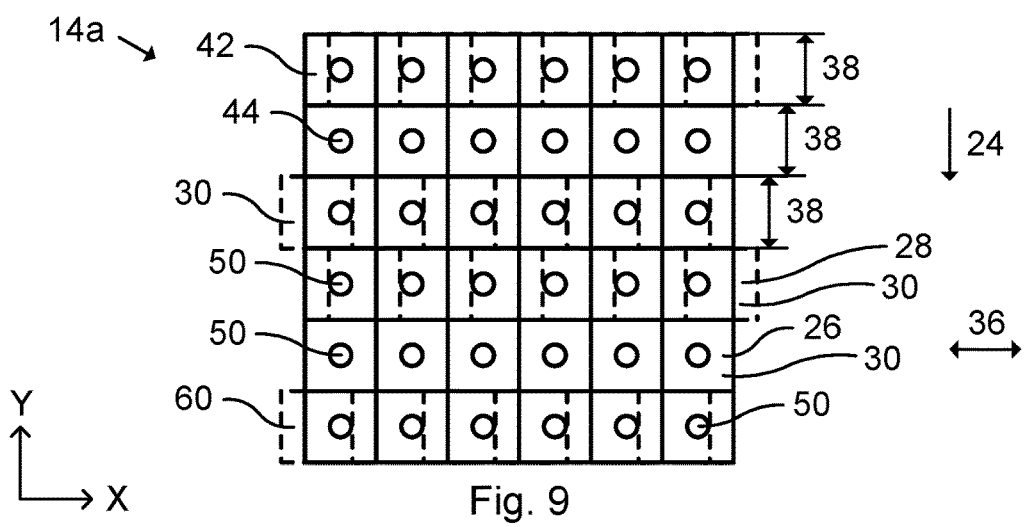
FIG. 9 schematically represents a top view of a further sensor unit.

FIG. 9 schematically represents a top view of a further sensor unit 14a. Mainly differences with respect to FIGS. 2 to 6 will be described. The sensor unit 14a in FIG. 9 comprises the conversion element 22a in FIG. 7 and the readout substrate 40 in FIG. 8. As shown in FIG. 9, each readout pixel 42 is connected to a unique associated imaging pixel 26, 28, 60 by means of a respective interconnection 44 at a connection position 50 on the charge collection electrode 30. Each first row 32 of first imaging pixels 26, each second row 34 of second imaging pixels 28 and each third row 62 of third imaging pixels 60 is aligned with a unique readout row 46 of readout pixels 42.

As shown in FIG. 9, the connection positions 50 for the first imaging pixels 26 are centered on the associated charge collection electrodes 30, the connection positions 50 for the second imaging pixels 28 are on the left (in FIG. 9) third of the associated charge collection electrodes 30, and the connection positions 50 for the third imaging pixels 60 are on the right third of the associated charge collection electrodes 30. Thus, only the connection positions 50 of the second imaging pixels 28 and the third imaging pixels 60 are offset with respect to the associated charge collection electrodes 30 in this example. The first imaging pixels 26 are centered with respect to the associated readout pixels 42.

The connection positions 50 in relation to the charge collection electrodes 30 are the same for all first imaging pixels 26, the connection positions 50 in relation to the charge collection electrodes 30 are the same for all second imaging pixels 28, and the connection positions 50 in relation to the charge collection electrodes 30 are the same for all third imaging pixels 60.

The readout substrate 40 of the type in FIGS. 3 and 8 can thus be used with each of the conversion element 22 in FIG. 2 and the conversion element 22a in FIG. 7.

FIGS. 2 and 4 illustrate two rows 32, 34 that are alternatingly arranged with two sets of imaging pixels 26, 28 offset from each other in a shifting direction 36. In an example, the offset can be between half (½) of the width 58 of the charge collection electrode 30 and half (½) of the width of the imaging pixels 26, 28. FIGS. 7 and 9 illustrate three rows 32, 34, 62 that are alternatingly arranged with three sets of imaging pixels 26, 28, 60 offset from each other in a shifting direction 36. In an example, each offset can be between a third (⅓) of the width 58 of the charge collection electrode 30 and a third (⅓) of the width of the imaging pixels 26, 28, 60. In similarly in another example (not shown), five rows can be alternatingly arranged with five sets of imaging pixels offset from each other in a shifting direction 36. Relative to FIGS. 7 and 9, the first additional row of the two additional rows can have imaging pixels with an offset between the offset of imaging pixels 26 and 60, and the second additional row of the two additional rows can have imaging pixels with an offset between the offset of imaging pixels 28 and 60. In an example, each offset can be between a fifth (⅕) of the width 58 of the charge collection electrode 30 and a fifth (⅕) of the width of the imaging pixels. While practically having a number of different offset rows greater than five (5) rows may not provide a significant benefit in resolution, the number of rows with different offsets does not need to be limited to 2, 3, or 5 different offset rows and distance between of those offsets does not need to be limited to be greater than a fifth (⅕) of the width 58 of the charge collection electrode 30 or a fifth (⅕) of the width of the imaging pixels. The number of rows with different offsets can be unlimited and distance between those offsets can also be infinitesimally small as long as the interconnection 44 of the readout pixel 42 is aligned with the connection position 50 on the charge collection electrode 30 of the imaging pixels 26, 28, 60.

Figure 10:
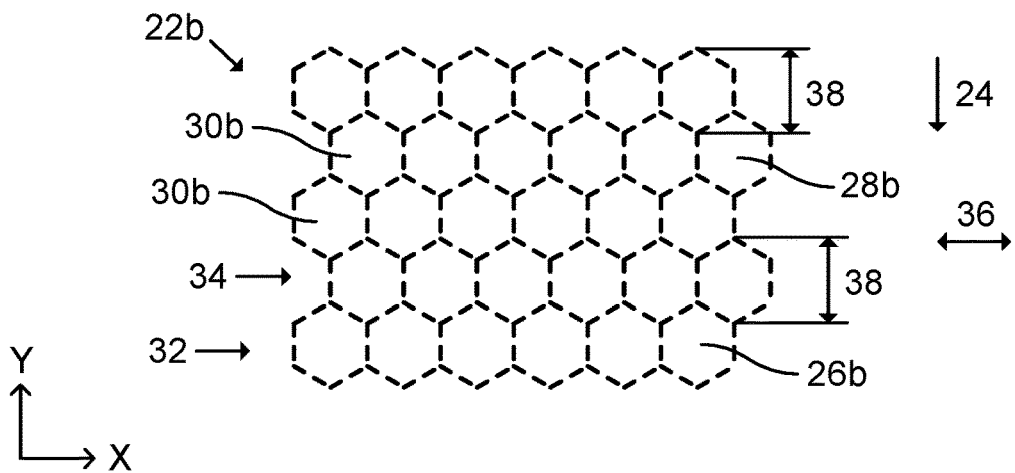
FIG. 10 schematically represents a top view of a further conversion element.

FIG. 10 schematically represents a top view of a further conversion element 22b. Mainly differences with respect to FIGS. 2 to 6 will be described. In this example, each imaging pixel 26b, 28b and its associated charge collection electrode 30b has a hexagonal shape. The imaging pixels 26b, 28b are arranged in a hexagonal grid. The first imaging pixels 26b and the second imaging pixels 28b have the same size. Also the associated charge collection electrodes 30b have the same size.

The second imaging pixels 28b are shifted half a width of the imaging pixels 26b, 28b from a position where the second imaging pixels 28b are aligned with the first imaging pixels 26b.

Figure 11:
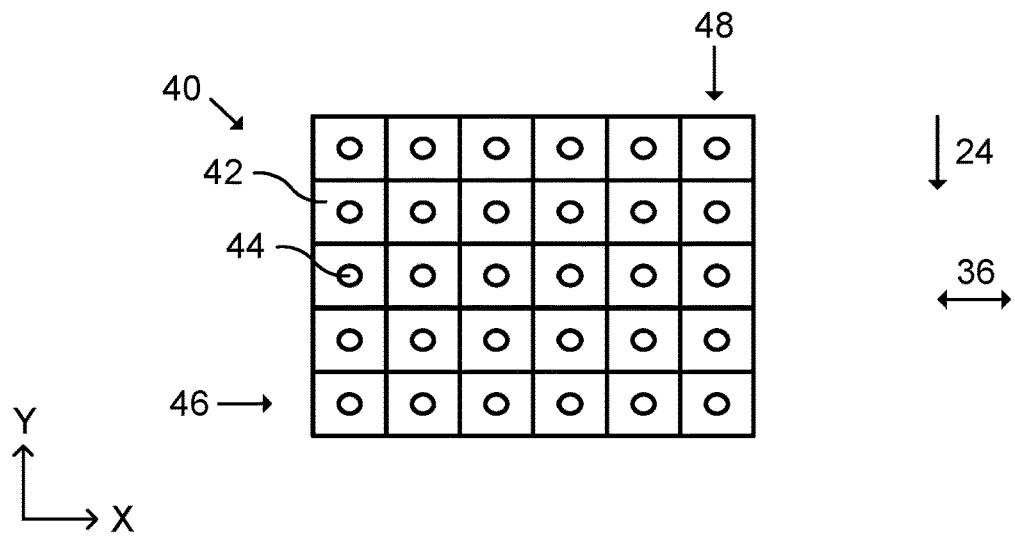
FIG. 11 schematically represents a top view of a readout substrate.

FIG. 11 schematically represents a top view of a readout substrate 40. The readout substrate 40 in FIG. 8 is of the same type as in FIG. 4. The readout substrate 40 has a regular matrix design (both along the rows and columns). However, the readout pixels 42 in FIG. 11 are rectangular having a width (parallel with the shifting direction 36) that is larger than a length (parallel with the scanning direction 24).

Figure 12:
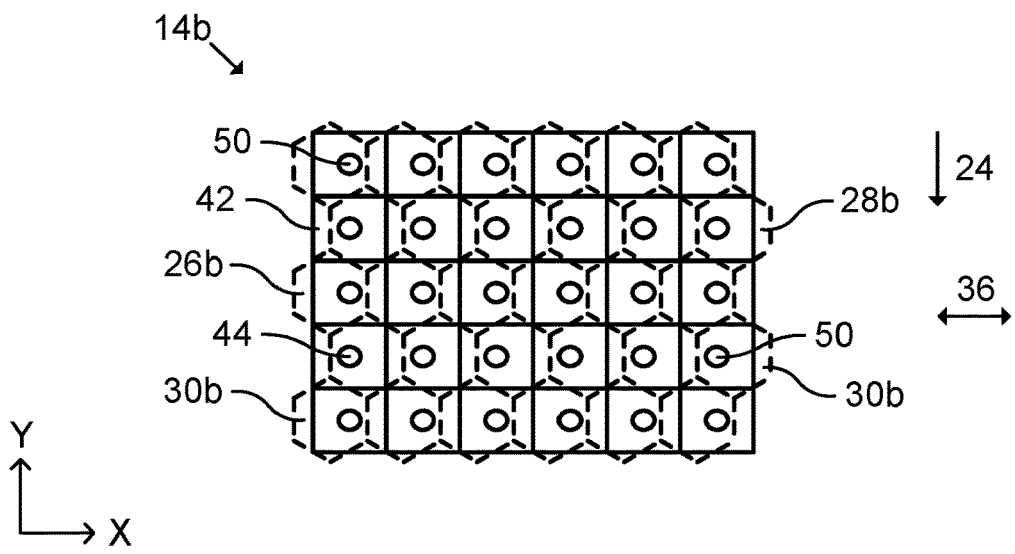
FIG. 12 schematically represents a top view of a further sensor unit.

FIG. 12 schematically represents a top view of a further sensor unit 14b. Mainly differences with respect to FIGS. 2 to 6 will be described. The sensor unit 14b in FIG. 12 comprises the conversion element 22b in FIG. 10 and the readout substrate 40 in FIG. 11. As shown in FIG. 12, each readout pixel 42 is connected to a unique associated imaging pixel 26b, 28b by means of a respective interconnection 44 at a connection position 50 on the charge collection electrode 30b. Each first row 32 of first imaging pixels 26b and each second row 34 of second imaging pixels 28b is aligned with a unique readout row 46 of readout pixels 42.

As shown in FIG. 12, the connection positions 50 for the first imaging pixels 26b are on the right (in FIG. 12) half of the associated charge collection electrodes 30b, and the connection positions 50 for the second imaging pixels 28b are on the left (in FIG. 12) half of the associated charge collection electrodes 30b. The connection positions 50 in relation to the charge collection electrodes 30b are the same for all first imaging pixels 26b, and the connection positions 50 in relation to the charge collection electrodes 30b are the same for all second imaging pixels 28b. During scanning of the object 20, the sampling frequency of the radiation detector 12 may be set such that at least one point per row of hexagonal imaging pixels 26b, 28b is obtained. In this example, electric signals generated by the imaging pixels 26b, 28b may be sampled at successive increments of movement of the sensor unit 14b in the scanning direction 24 equal to or less than 75% of the length 38 of each imaging pixel 26b, 28b in the scanning direction 24.

Figure 13:
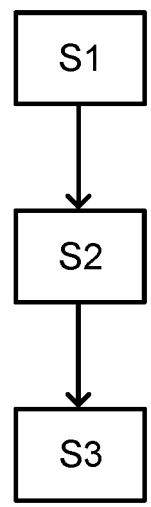
FIG. 13 is a flowchart outlining the general steps of a method of manufacturing a sensor unit.

FIG. 13 is a flowchart outlining the general steps of a method of manufacturing a sensor unit 14, 14a, 14b. The method comprises a step S1 of providing a conversion element 22, 22a, 22b comprising a plurality of imaging pixels 26, 26b, 28, 28b, 60, each imaging pixel 26, 26b, 28, 28b, 60 being configured to directly convert radiation into an electrical charge, each imaging pixel 26, 26b, 28, 28b, 60 comprising a charge collection electrode 30, 30b, and the imaging pixels 26, 26b, 28, 28b, 60 comprising first imaging pixels 26, 26b and second imaging pixels 28, 28b. The method further comprises a step S2 of providing a readout substrate 40 comprising a plurality of readout pixels 42 arranged in a grid. The method further comprises a step S3 of connecting each readout pixel 42 to an associated imaging pixel 26, 26b, 28, 28b, 60 by means of an interconnection 44 at a connection position 50 on the charge collection electrode 30, 30b, wherein the second imaging pixels 28, 28b are shifted in a shifting direction 36 relative to the first imaging pixels 26, 26b; and wherein the connection positions 50 in relation to the charge collection electrodes 30, 30b are different between the first imaging pixels 26, 26b and the second imaging pixels 28, 28b.

Figure 14:
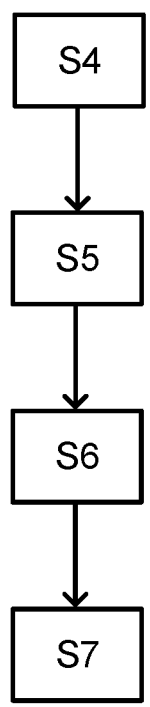
FIG. 14 is a flowchart outlining the general steps of a method of using a sensor unit.

FIG. 14 is a flowchart outlining the general steps of a method of using a sensor unit 14, 14a, 14b. The method comprises a step S4 of providing a sensor unit 14, 14a, 14b comprising a conversion element 22, 22a, 22b comprising a plurality of imaging pixels 26, 26b, 28, 28b, 60, each imaging pixel 26, 26b, 28, 28b, 60 being configured to directly convert radiation into an electrical charge, each imaging pixel 26, 26b, 28, 28b, 60 comprising a charge collection electrode 30, 30b, and the imaging pixels 26, 26b, 28, 28b, 60 comprising first imaging pixels 26, 26b and second imaging pixels 28, 28b; and a readout substrate 40 comprising a plurality of readout pixels 42 arranged in a grid, each readout pixel 42 being connected to an associated imaging pixel 26, 26b, 28, 28b, 60 by means of an interconnection 44 at a connection position 50 on the charge collection electrode 30, 30b; wherein the second imaging pixels 28, 28b are shifted in a shifting direction 36 relative to the first imaging pixels 26, 26b; and wherein the connection positions 50 in relation to the charge collection electrodes 30, 30b are different between the first imaging pixels 26, 26b and the second imaging pixels 28, 28b.

The method further comprises a step S5 of moving the sensor unit 14, 14a, 14b in a scanning direction 24 substantially perpendicular to the shifting direction 36. The method further comprises a step S6 of generating electric signals responsive to radiation onto the imaging pixels 26, 26b, 28, 28b, 60. The method further comprises a step S7 of sampling the electric signals at successive increments of movement of the sensor unit 14, 14a, 14b in the scanning direction 24 equal to or less than a length 38 of each imaging pixel 26, 26b, 28, 28b, 60 in the scanning direction 24.

The sensor unit 14, 14a, 14b disclosed can be used to generate effective high resolution pixels also referred to as super resolution pixels 70, 80, 90, 92, 94, 96. Each super resolution pixel 70, 80, 90, 92, 94, 96 can have an effective width 76, 86 smaller than the imaging pixel width 68 and/or an effective length 78, 88 that is smaller than the imaging pixel length 38. In an example, each super resolution pixel 70, 80, 90, 92, 94, 96 is configured to contain unique information (i.e., signal and/or energy information) relative to the imaging pixels from which the super resolution pixel 70, 80, 90, 92, 94, 96 is derived. The effective width 76, 86 of the super resolution pixel 70, 80, 92, 96 can be determined by the number of offsets the imaging pixels 26, 28, 60 have from neighboring imaging pixels 26, 28, 60 in the scanning direction 24 and the distance between those offsets. The effective length 78, 88 of the super resolution pixel 90, 92, 94, 96 can be determined by the speed of the sensor unit 14, 14a, 14b relative to the object 20 in the scanning direction 24 and the processing speed of the readout circuitry (including the readout pixels 42 on the readout substrate 40). For example, the effective length 78, 88 of the super resolution pixel 90, 92, 94, 96 can be determined by a sampling rate per imaging pixel row 32, 34, 62.

Figure 15:
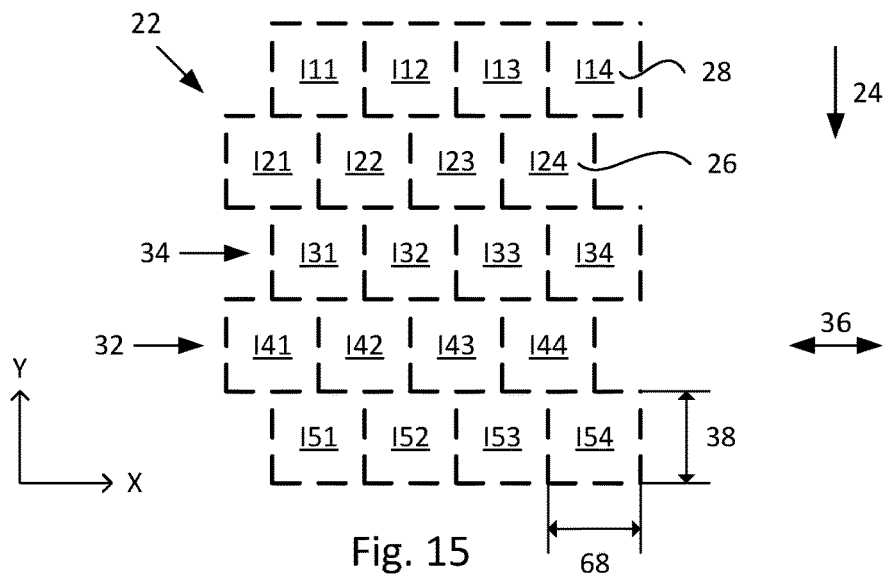
FIG. 15 schematically represents a top view of a conversion element.

FIGS. 15-20 schematically represent different views and layers of a sensor unit 14 with one offset. FIG. 15 schematically represents a top view of a conversion element 22 of one of the sensor units 14, similar to FIG. 2. Each imaging pixel 26, 28 has a width 68 similar to or larger than the width 58 of the charge collection electrode 30 in the shifting direction 36 and a length 38 in the scanning direction 24. As shown, each second imaging pixel 28 of a second row 34 is offset with respect to at least one neighboring first imaging pixel 26 of a first row 32 by approximately a half (½) of the width 68 of the imaging pixels 26, 28 in the shifting direction 36. For illustrative purposes, each imaging pixels 26, 28 is labelled relative to its position in the conversion element 22 with an "I" (for imaging pixel) followed by a row and column numeral. Although imaging pixels 26, 28 are offset from neighboring imaging pixels 26, 28 in the scanning direction 24, the column numeral indicates the column of the readout pixel 42 coupled to the imaging pixels 26, 28. For example, the top left imaging pixel 28 is labelled I11 as it is in the first row and first column of the corresponding readout pixel 42. Other imaging pixels 26, 28 are similarly labelled from I11 to I54 (imaging pixel in the fifth row and fourth column).

Figure 16:
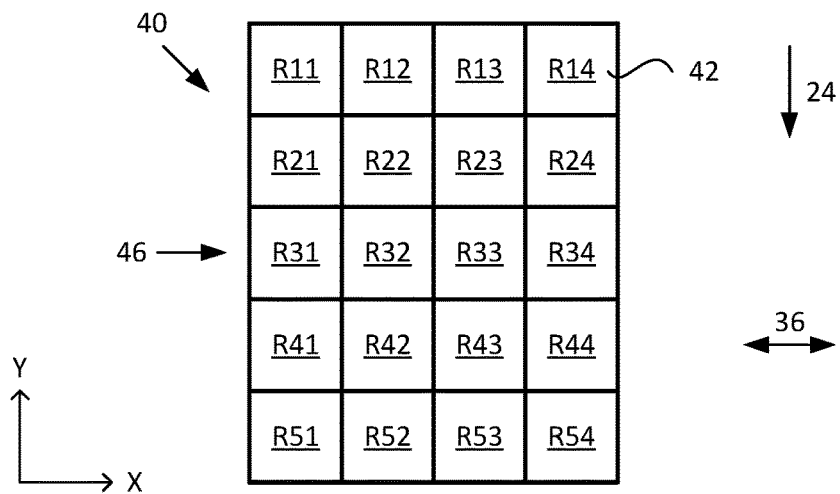
FIG. 16 schematically represents a top view of a readout substrate.
Figure 17:
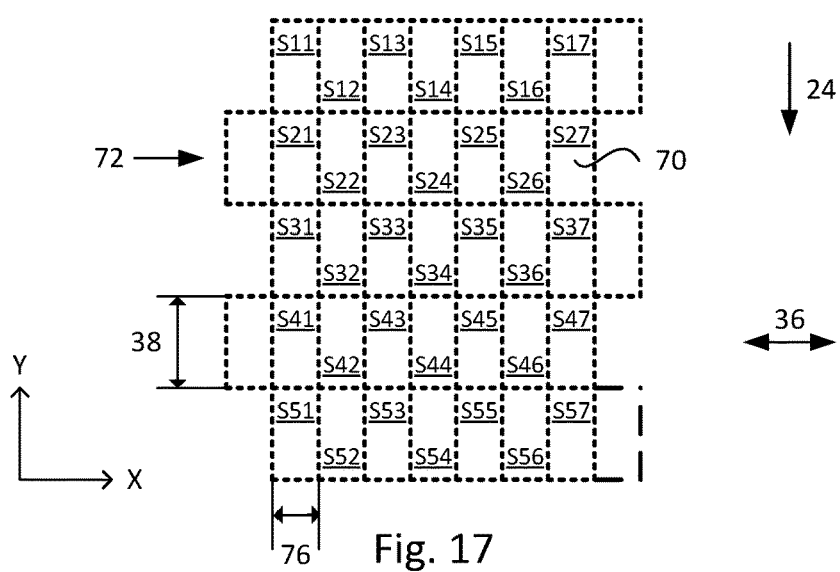
FIG. 17 schematically represents a top view of conceptual super resolution pixels overlaid on a sensor unit.

FIG. 16 schematically represents a top view of a readout substrate 40 of the same sensor unit 14 comprising the conversion element 22, similar to FIG. 3. Similarly, for illustrative purposes, each readout pixel 42 is labelled relative to its position in the sensor unit 14 with an "R" (for readout pixel) followed by a row and column numeral. For example, the top left readout pixel 42 is labelled R11 as it is in the first row and first column. Other readout pixels 42 are similarly labelled from R11 to R54 (readout pixel in the fifth row and fourth column). FIG. 17 schematically represents a top view of conceptual super resolution pixels 70 overlaid on a sensor unit 14. The super resolution pixels 70 can be represented by rows 72. Each super resolution pixel 70 has a width 76 that is a fraction of the imaging pixel width 68 in the shifting direction 36. In an example, the super resolution pixel width 76 is less than 75 or 60% of the imaging pixel width 68. The effective length of the super resolution pixel 70 can be determined by a sampling rate per imaging pixel row 32, 34. FIG. 17 illustrates sampling rate of one sample per imaging pixel row 32, 34, so the effect length of the super resolution pixel 70 is similar to the imaging pixel length 38. Each super resolution pixel 70 is derived or calculated from information captured from at least two imaging pixels 26, 28 in the scanning direction 24. For a second imaging pixel 28 that has one offset with respect to at least one neighboring first imaging pixel 26 that is approximately a half (½) of the imaging pixel width 68, the super resolution pixel width 76 can be a half (½) of the imaging pixel width 68.

For illustrative purposes, each super resolution pixel 70 is labelled relative to its position in the sensor unit 14 with an "S" (for super resolution pixel) followed by a row and column numeral. For example, the top left super resolution pixel 70 is labelled S11 as it is in the first row and first column. Other super resolutions pixel 70 are similarly labelled from S11 to S57 (super resolutions pixel in the fifth row and seventh column).

Figure 18:
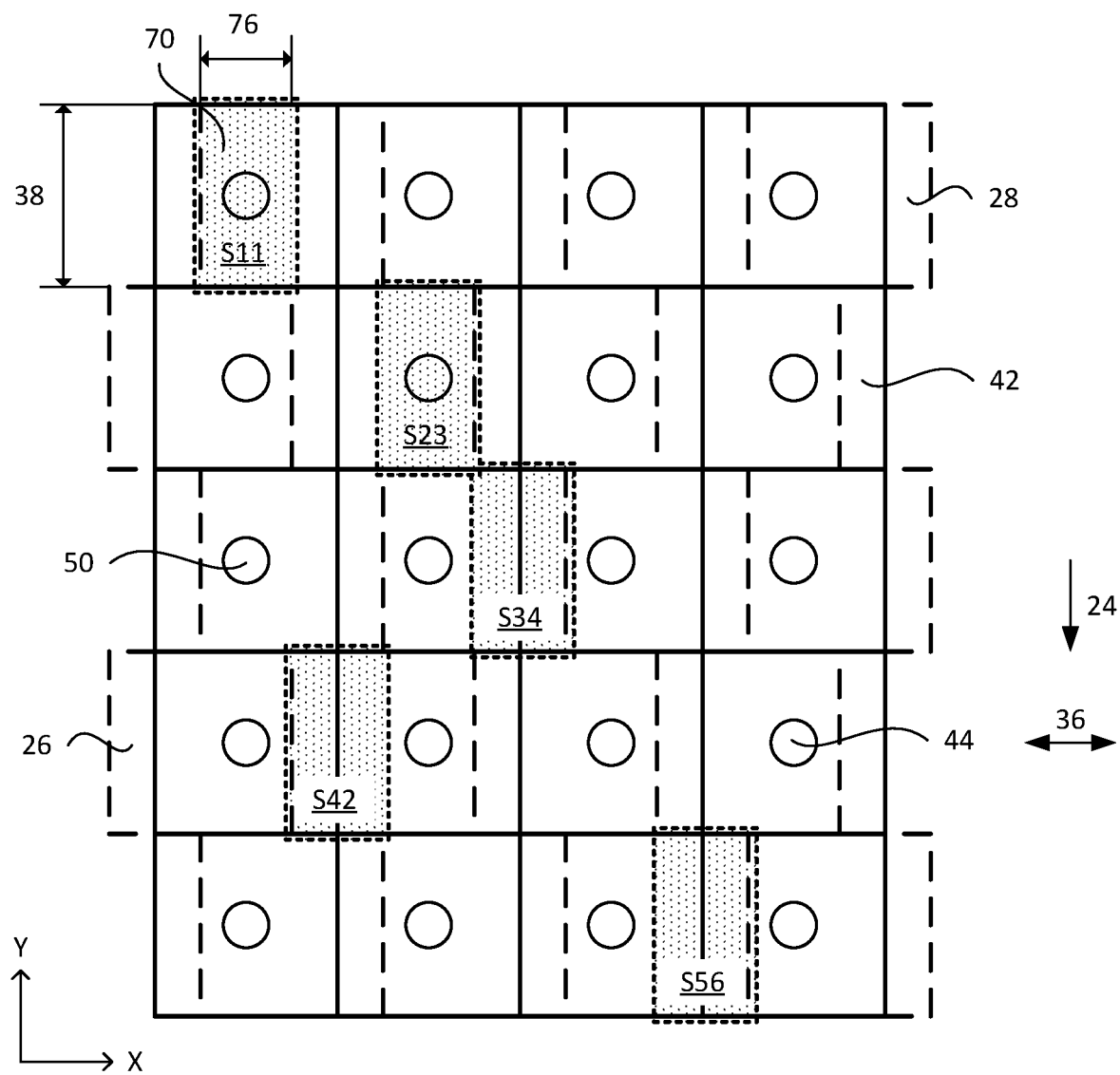
FIG. 18 schematically represents a top view of conceptual super resolution pixels overlaid on a sensor unit.

FIG. 18 schematically represents a top view of the same sensor unit 14 comprising the conversion element 22 in FIG. 15, the readout substrate 40 in FIG. 16, and the conceptual super resolution pixels 70 in FIG. 17. Each super resolution pixel 70 is derived or calculated from information captured from at least two imaging pixels 26, 28 (e.g., adjacent imaging pixels in the scanning direction 24) in two different rows 32, 34 (e.g., adjacent rows) over at least two samples. For example, super resolution pixel S23 can be derived or calculated from information sensed from imaging pixels I12 and I22 (i.e., using information from prior sample and current samples) or from imaging pixels I22 and I32 (i.e., using information from current and later samples) in subsequent samples. Half (½) of the super resolution pixels 70 can be derived or calculated from information captured from two imaging pixels 26, 28 in the same column. For example, information for super resolution pixel S23 can be sensed by imaging pixel I12 and I22 (in the same imaging pixel column) and their electrical signals are captured in readout pixel R12 and R22 (in the same readout pixel column). And the other half (½) of the super resolution pixel 70 can be derived or calculated from information captured from two imaging pixels 26, 28 in different imaging pixel columns. For example, super resolution pixel S34 can be sensed by imaging pixel I23 and I32 (in different imaging pixel columns) and their electrical signals are captured in readout pixel R23 and R32 (in different readout pixel columns).

Conventionally, resolution has been limited to the imaging pixel size and/or pixel pitch, where pixel pitch is the distance between pixels. The sensor unit 14 can provide a resolution higher than the imaging pixel size. During scanning of the object 20, a point in the imaged object is sampled multiple times as the point travels across multiple imaging pixels 26, 28 of the sensor unit 14 in the scanning direction 24. The sensor unit 14 can be used to provide a determination or finer granularity of a point's location within the imaging pixel 26, 28 with multiple samples. For example, if a point of the object 20 travels across the right half of imaging pixel (e.g., I11) in a first row that same point travels across the left half of imaging pixel (e.g., I22) in a successive sample or increment of movement of the sensor unit 14

(or in a second row in a subsequent sample). Similarly, if a point of the object 20 travels across the left half of imaging pixel (e.g., I11) in a first row that same point in travels across the right half of imaging pixel (e.g., I21) in a successive sample or increment of movement of the sensor unit 14 (or in a second row in a subsequent sample). During a first sample or increment of movement of the sensor unit 14, the imaging pixel (e.g., I11) in a first row may generate electric signals responsive to radiation representing the point of the object. During a second sample or increment of movement of the sensor unit 14, a neighboring imaging pixel (e.g., I21 or I22) in a second row may generate electric signals responsive to radiation representing the point of the object.

Because a super resolution pixel 70 (e.g., S21) only includes a fraction (e.g., ½) of the energy generated by the imaging pixel (e.g., I11) in the first row or first sample, the collected energy may be multiplied by the fraction representing the relative area of the imaging pixel 26, 28 overlapping the area represented by the super resolution pixel 70. Similarly, because a super resolution pixel 70 (e.g., S21) only includes a fraction (e.g., ½) of the energy generated by the imaging pixel (e.g., I21) in the second row or second sample, the collected energy may be multiplied by the fraction representing the relative area of the imaging pixel 26, 28 overlapping the area represented by the super resolution pixel 70. Mathematically, the super resolution pixel energy (srpe) can be represented as the energy (ip1$e$) of the imaging pixel 26, 28 in the first row captured in a first sample multiplied by fraction (ip1$f$) of the imaging pixel area in the first row overlapping the area represented by the super resolution pixel 70 and the energy (ip2$e$) of the imaging pixel 26, 28 in the second row captured in a second sample multiplied by fraction (ip2$f$) of the imaging pixel area in the second row overlapping the area represented by the super resolution pixel 70 (e.g., srpe=ip1$f$*ip1$e$+ip2$f$*ip2$e$ or srpe=½*ip1$e$+½*ip2$e$). If the fraction (ip1$f$) of the imaging pixel area in the first row overlapping the area represented by the super resolution pixel 70 and the fraction (ip2$f$) of the imaging pixel area in the second row overlapping the area represented by the super resolution pixel 70 are similar or equal (ip1$f$=ip2$f$), then the super resolution pixel energy (srpe) of each super resolution pixel can be represented by a gain factor (gf) multiplied by the energy (ip1$e$) of the imaging pixel 26, 28 in the first row plus the energy (ip2$e$) of the imaging pixel 26, 28 in the second row (srpe=gf*(ip1$e$+ip2$e$)). Thus the super resolution pixel energy (srpe) of the super resolution pixels can be adjusted for the sensor unit 14 with the gain factor (gf).

The radiation energy representing the point of the object is fully represented in a super resolution pixel 70 (e.g., S23). While a neighboring super resolution pixel 70 (e.g., S22 and S24) in the shifting direction 36 contains half (½) the radiation energy representing the point of the object as one imaging pixel 26, 28 (e.g., in the first row 32 or the second row 34 in two samples) registering radiation energy representing the point of the object but the second or subsequent imaging pixel 26, 28 (in the two samples) does not register radiation energy representing the point of the object. Non-neighboring super resolution pixel 70 (e.g., S21 and S25) in the shifting direction 36 (i.e., with at least one super resolution pixel of separation) does not contain the radiation energy representing the point of the object as none of the imaging pixels 26, 28 register radiation energy representing the point of the object in the two samples (or other samples). Thus, neighboring super resolution pixel 70 in the shifting direction 36 may sense or register a portion of the radiation energy representing the point of the object even when the neighboring super resolution pixel 70 does not overlap with the point of the object on the sensor unit 14.

During scanning of the object 20, the sampling frequency of the radiation detector 12 may be set such that at least one point per row of imaging pixels 26, 28 is obtained. Electric signals generated by the imaging pixels 26, 28 may be sampled at successive increments of movement of the sensor unit 14 in the scanning direction 24. Multiple super resolution pixels 70 (e.g., S11, S21, S31, S41, and S51) in the scanning direction 24 representing the point of the object may be averaged together, which can also improve the resolution of the point of the object. In an example, the sensor unit 14 can use each of the super resolution pixels 70 (e.g., S11, S21, S31, S41, and S51) in the scanning direction 24 representing the point of the object. In another example, the sensor unit 14 can use subset of the super resolution pixels 70 (e.g., S11, S21, S31, S41, or S51) in the scanning direction 24 representing the point of the object, such that each imaging pixel 26, 28 is only represented or weighted once in super resolution pixels 70 in the scanning direction 24.

Figure 19:
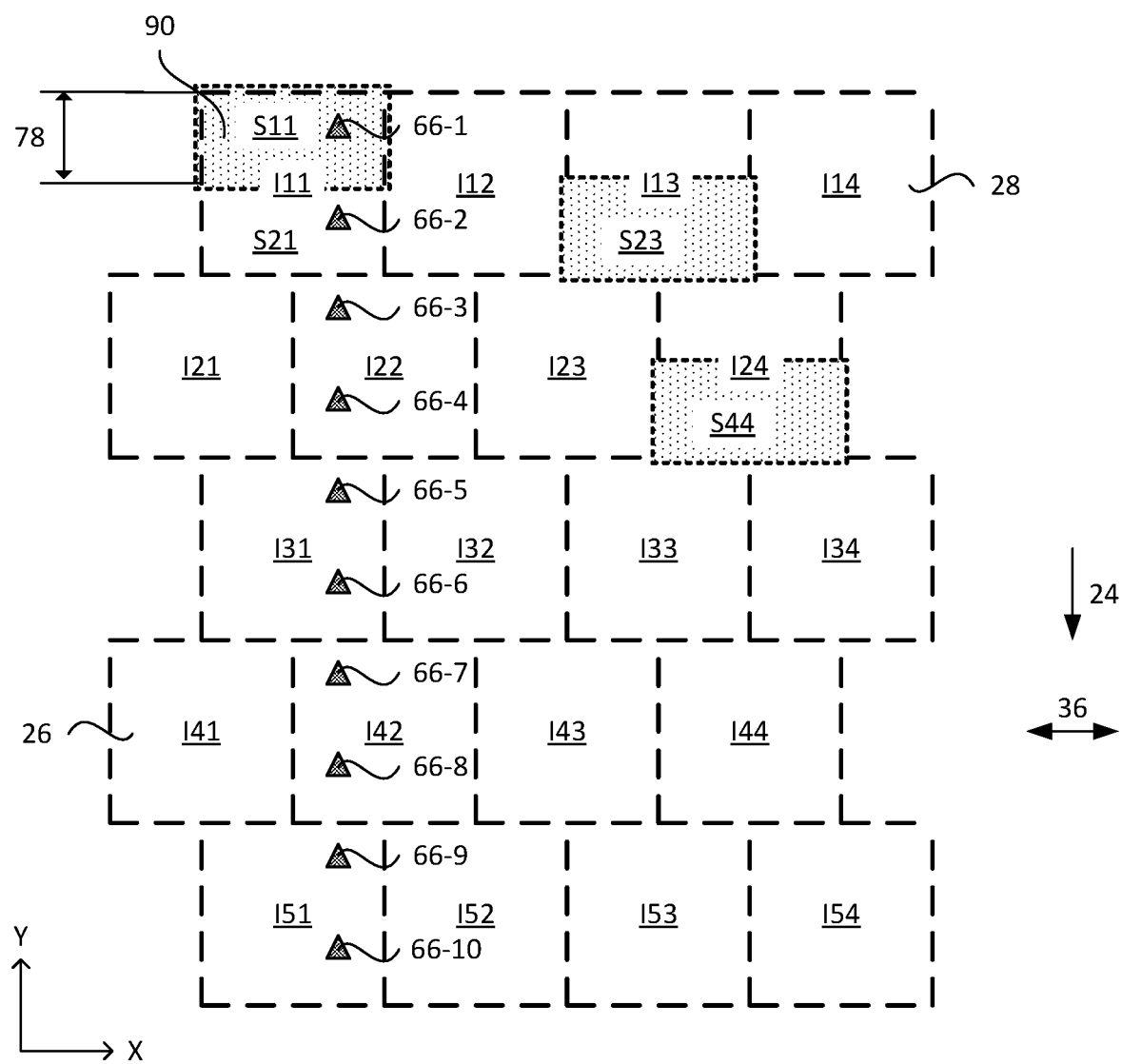
FIG. 19 schematically represents a top view of a point of an object and conceptual super resolution pixels overlaid on a conversion element over different sampling times.

FIG. 19 schematically represents a top view of a point 66 of an object 20 represented on a conversion element 22 and conceptual super resolution pixels 90 overlaid with a sampling rate of two samples per imaging pixel row 32, 34 with an object moving uniformly in the scanning direction 24. In this example, information (i.e., signal and/or energy information) about the point 66 of the object 20 can be captured by the same imaging pixel 26, 28 twice, so two super resolution pixels 90 occur in each imaging pixel 26, 28. For example, during a first sample, information about a point 66-1 of an object 20 may be captured in a top half of the imaging pixel I11 and is represented as super resolution pixel S11. In a successive increment of movement or second sample, the information about the point 66-2 of the object 20 may be captured in a bottom half of the imaging pixel I11 and is represented as super resolution pixel S21. In another successive increment of movement or third sample, the information about the point 66-3 of the object 20 may be captured in a top half of the imaging pixel I22 and represented as super resolution pixel S32. In another successive increment of movement or fourth sample, the information about the point 66-4 of the object 20 may be captured in a bottom half of the imaging pixel I22 and represented as super resolution pixel S42. The pattern continues where each imaging pixel I11, I22, I31, I42, I51 samples the point 66-1 to 66-10 of the object 20 twice. Prior super resolution pixel information and a difference between neighboring samples in the scanning direction 24 can be used to generate or extract information for a super resolution pixel 90 with an effective length 78 that is smaller than the imaging pixel 38. For example, the information (i.e., signal and/or energy information) for the super resolution pixel 90 can be calculated by comparing a current sample captured by the imaging pixel 26, 28 with a prior or subsequent sample captured by the imaging pixel 26, 28 in the scanning direction 24 plus the information for the super resolution pixels 90 in the same relative position (in the scanning direction 24) in a prior or subsequent imaging pixel 26, 28 or samples. With a sampling rate of two samples per imaging pixel row 32, 34, the effective length 78 as shown in FIG. 19 is approximately a half (½) of the imaging pixel length 38. Due to the offset between the imaging pixel 26, 28 in the imaging pixel row 32, 34 relative to the readout pixels 42 in the readout pixel rows 46, a resulting image (without using another approach or correction) may be skewed within an imaging pixel width 68 relative to the features of the actual object 20.

Figure 20:
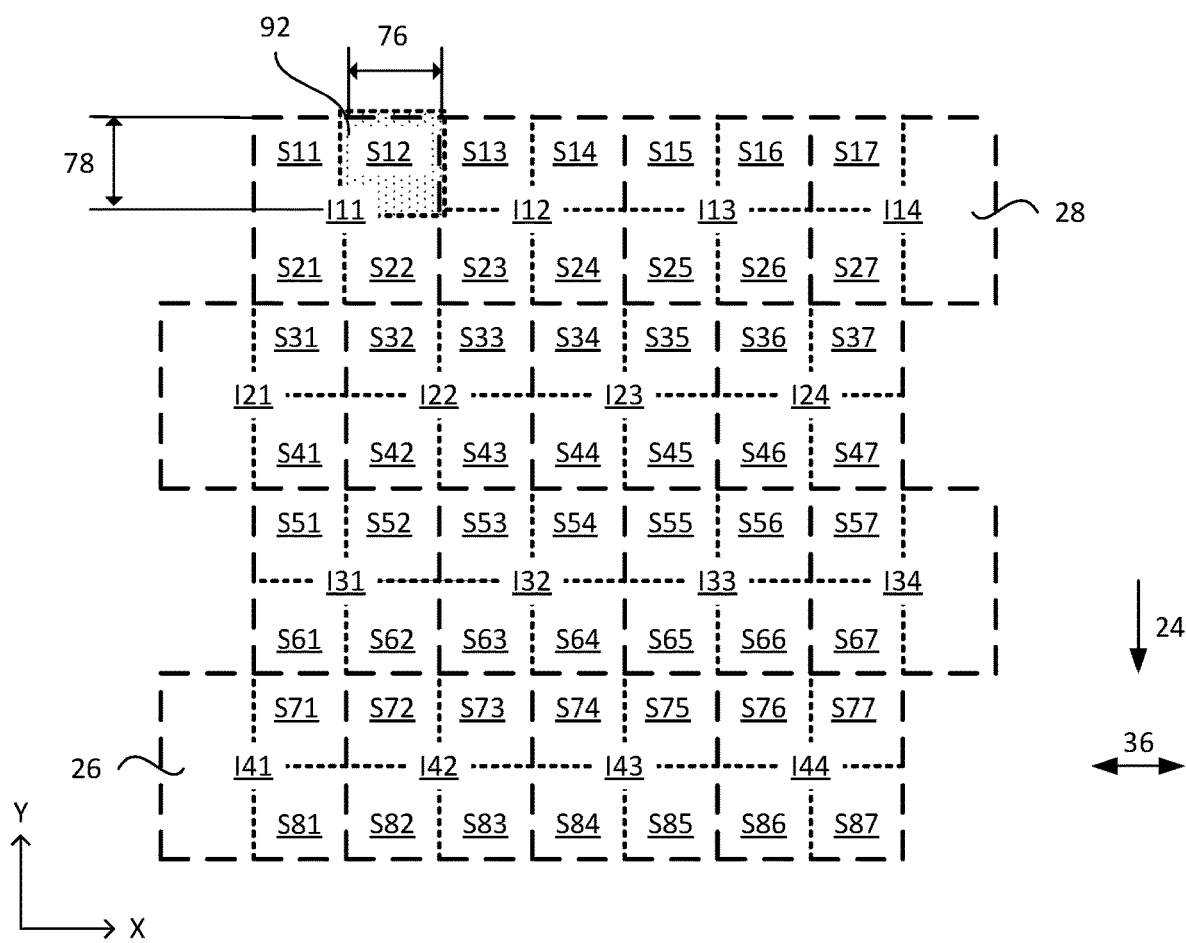
FIG. 20 schematically represents a top view of conceptual super resolution pixels overlaid on a sensor unit.

FIG. 20 schematically represents a top view of conceptual super resolution pixels overlaid on a sensor unit where each super resolution pixel 92 has an effective width 76 smaller than the imaging pixel width 68 and an effective length 78 that is smaller than the imaging pixel length 38. FIG. 20 combines the approach shown and described relative to FIGS. 17-18 to obtain a super resolution pixel 92 that has an effective width 76 smaller than the imaging pixel width 68 with the approach shown and described relative to FIG. 19 to obtain a super resolution pixel 92 has an effective length 78 that is smaller than the imaging pixel length 38. For example, one imaging pixel 26, 28 (e.g., I11) can be represented by four super resolution pixels 92 (e.g., S11, S12, S21, and S22) or four super resolution pixels 92 can be overlaid on a single imaging pixel 26, 28 thus providing greater resolution than the native imaging pixel 26, 28.

Figure 21:
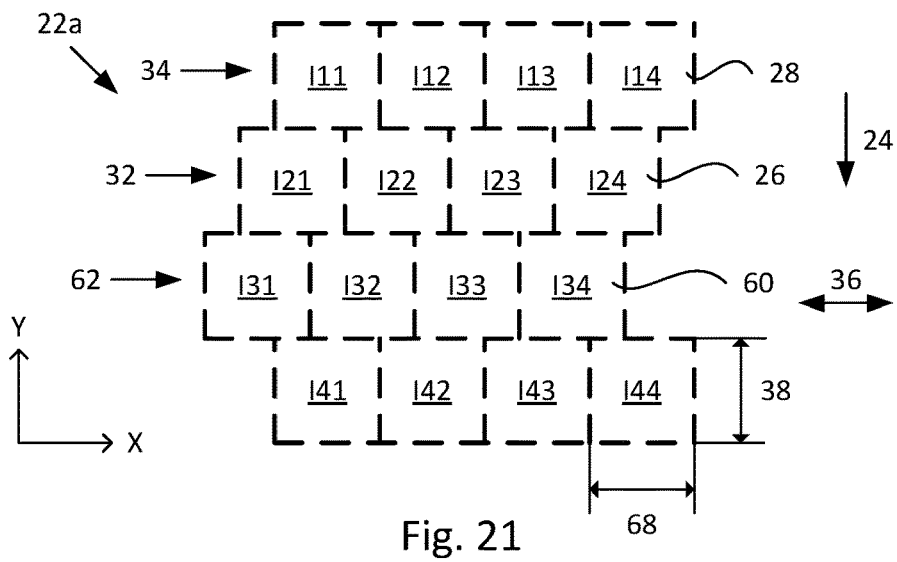
FIG. 21 schematically represents a top view of a conversion element.

FIGS. 21-26 schematically represent different views and layers of a sensor unit 14a with two offsets. FIG. 21 schematically represents a top view of a conversion element 22a of one of the sensor units 14a, similar to FIG. 7 but with only four rows of imaging pixels 26, 28, 60. Each imaging pixel 26, 28, 60 has a width 68 similar to or larger than the width 58 of the charge collection electrode 30 in the shifting direction 36 and a length 38 in the scanning direction 24. As shown, each second imaging pixel 28 of a second row 34 is offset with respect to at least one neighboring first imaging pixel 26 of a first row 32 by approximately a third (⅓) of the width 68 of the imaging pixels 26, 28, 60 in the shifting direction 36. Each third imaging pixel 60 of a third row 62 is offset with respect to at least one neighboring first imaging pixel 26 of a first row 32 by approximately a third (⅓) of the width 68 of the imaging pixels 26, 28, 60 in the shifting direction 36. For illustrative purposes, each imaging pixel 26, 28, 60 is labelled relative to its position in the conversion element 22a with an "I" (for imaging pixel) followed by a row and column numeral. Although imaging pixels 26, 28, 60 are offset from neighboring imaging pixels 26, 28, 60 in the scanning direction 24, the column numeral indicates the column of the readout pixel 42 coupled to the imaging pixels 26, 28, 60. For example, the top left imaging pixel 28 is labelled I11 as it is in the first row and first column of the corresponding readout pixel 42. Other imaging pixels 26, 28 are similarly labelled from I11 to I44 (imaging pixel in the fourth row and fourth column).

Figure 22:
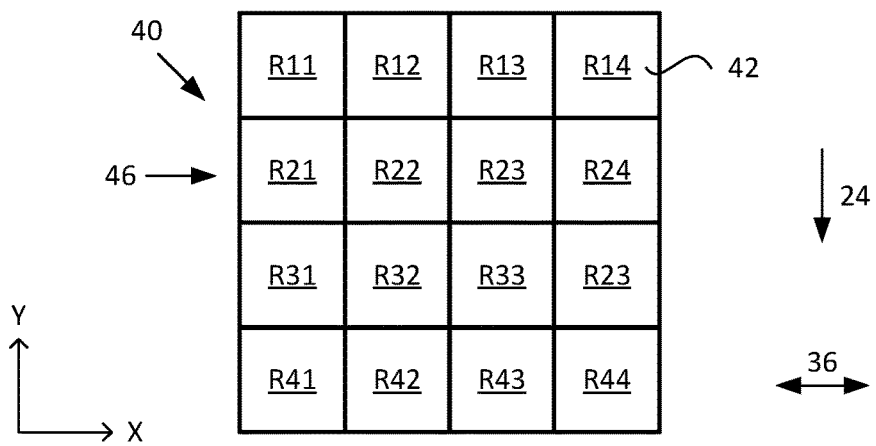
FIG. 22 schematically represents a top view of a readout substrate.

FIG. 22 schematically represents a top view of a readout substrate 40 of the same sensor unit 14a comprising the conversion element 22a, similar to FIG. 8 but with only four rows of readout pixels 42. Similarly, for illustrative purposes, each readout pixel 42 is labelled relative to its position in the sensor unit 14a with an "R" (for readout pixel) followed by a row and column numeral. For example, the top left readout pixel 42 is labelled R11 as it is in the first row and first column. Other readout pixels 42 are similarly labelled from R11 to R44 (readout pixel in the fourth row and fourth column).

Figure 23:
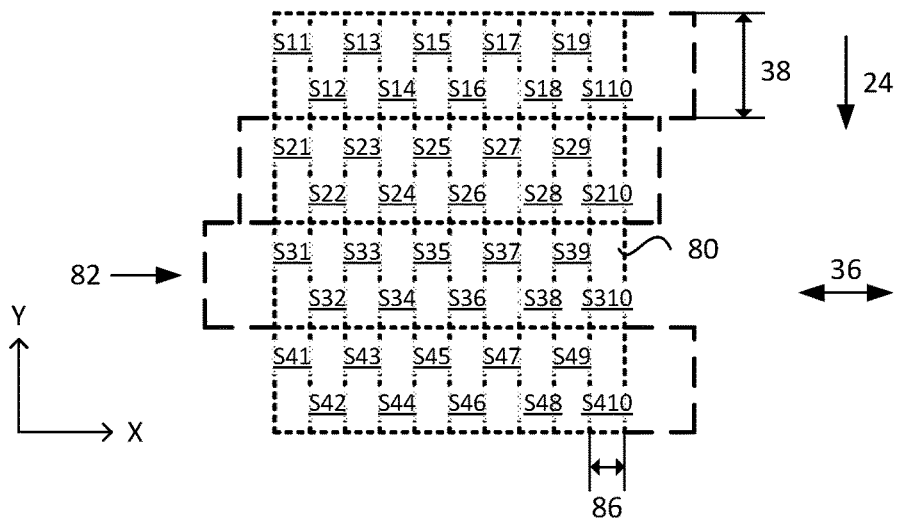
FIG. 23 schematically represents a top view of conceptual super resolution pixels overlaid on a sensor unit.

FIG. 23 schematically represents a top view of conceptual super resolution pixels 80 overlaid on a sensor unit 14a. The super resolution pixels 80 can be represented by rows 82. Each super resolution pixel 80 has a width 86 that is a fraction of the imaging pixel width 68 in the shifting direction 36. In an example, the super resolution pixel width 86 is less than 50 or 40% of the imaging pixel width 68. The effective length of the super resolution pixel 80 can be determined by a sampling rate per imaging pixel row 32, 34, 62. FIG. 23 illustrates sampling rate of one sample per imaging pixel row 32, 34, 62, so the effect length of the super resolution pixel 80 is similar to the imaging pixel length 38. Each super resolution pixel 80 is derived or calculated from information captured from at least three imaging pixels 26, 28, 60 in the scanning direction 24. For a first imaging pixel 26, second imaging pixel 28, and third imaging pixels 60 that each have an offset with each other that is approximately a third (⅓) of the imaging pixel width 68, the super resolution pixel width 86 can be a third (⅓) of the imaging pixel width 68.

For illustrative purposes, each super resolution pixel 80 is labelled relative to its position in the sensor unit 14a with an "S" (for super resolution pixel) followed by a row and column numeral. For example, the top left super resolution pixel 80 is labelled S11 as it is in the first row and first column. Other super resolutions pixel 80 are similarly labelled from S11 to S410 (super resolutions pixel in the fourth row and tenth column).

Figure 24:
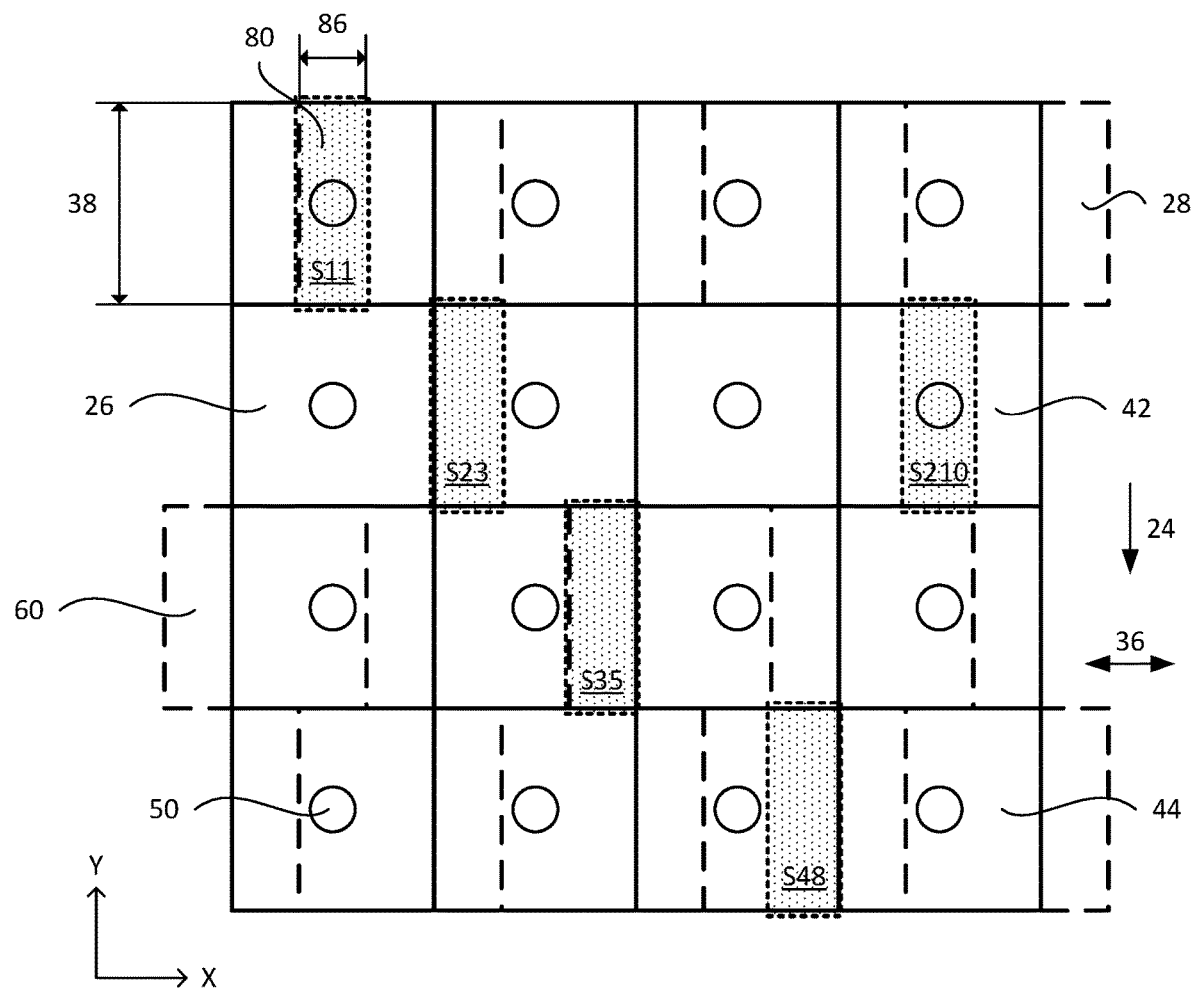
FIG. 24 schematically represents a top view of conceptual super resolution pixels overlaid on a sensor unit.

FIG. 24 schematically represents a top view of the same sensor unit 14a comprising the conversion element 22a in FIG. 21, the readout substrate 40 in FIG. 22, and the conceptual super resolution pixels 80 in FIG. 23. Each super resolution pixel 80 is derived or calculated from information captured from at least three imaging pixel 26, 28, 60 (e.g., adjacent imaging pixels in the scanning direction 24) in three different rows 32, 34, 62 (e.g., adjacent rows) over at least three samples. For example, super resolution pixel S35 can be derived or calculated from information sensed from imaging pixel I12, I22, and I33 (i.e., using information from prior sample and current samples) or from imaging pixels I22, I33, and I42 (i.e., using information from prior, current, and later samples) or from imaging pixels I33, I42, and I52 (not shown) (i.e., using information from current and later samples) in subsequent samples. A third (⅓) of the super resolution pixels 80 can be derived or calculated from information captured from three imaging pixel 26, 28, 60 in the same column. For example, information for super resolution pixel S31 can be sensed by imaging pixel I11, I21, I31 (in the same imaging pixel column) and their electrical signals are captured in readout pixel R11, R21, and R31 (in the same readout pixel column). And the other two thirds (⅔) of the super resolution pixel 80 can be derived or calculated from information captured from imaging pixels 26, 28, 60 in two different imaging pixel columns. For example, super resolution pixel S33 can be sensed by imaging pixel I11 (in a first column) and imaging pixels I22 and I32 (in a second column) and their electrical signals are captured in readout pixel R11 (in a first column) and readout pixels R22 and R32 (in a second column).

During scanning of the object 20, a point in the imaged object is sampled multiple times as the point travels across multiple imaging pixels 26, 28, 60 of the sensor unit 14a in the scanning direction 24. The sensor unit 14a can be used to provide a determination or finer granularity of a point's location within the imaging pixel 26, 28, 60 with multiple samples. For example, if a point of the object 20 travels across the right third of imaging pixel (e.g., I11) in a first row that same point travels across the left third of imaging pixel (e.g., I22) in a successive sample or increment of movement of the sensor unit 14a (or in a second row in a subsequent sample) and that same point also travels across the center third of imaging pixel (e.g., I32) in a successive sample or increment of movement of the sensor unit 14a (or in a third row in a subsequent sample). A point of the object 20 travels across the left third of an imaging pixel, the middle third of an imaging pixel, and a right third of an imaging pixel for each super resolution pixel 80 in successive samples or increments of movement of the sensor unit 14a. During a first sample or increment of movement of the sensor unit 14a, the imaging pixel (e.g., I11) in a first row may generate electric signals responsive to radiation representing the point of the object. During a second sample or increment of movement of the sensor unit 14a, a neighboring imaging pixel (e.g., I21 or I22) in a second row may generate electric signals responsive to radiation representing the point of the object. During a third sample or increment of movement of the sensor unit 14a, a neighboring imaging pixel (e.g., I31 or I32) in a third row may generate electric signals responsive to radiation representing the point of the object.

Because a super resolution pixel 80 (e.g., S31) only includes a fraction (e.g., ⅓) of the energy generated by the imaging pixel (e.g., I11) in the first row or first sample, the collected energy may be multiplied by the fraction representing the relative area of the imaging pixel 26, 28, 60 overlapping the area represented by the super resolution pixel 80. Similarly, because a super resolution pixel 80 (e.g., S31) only includes a fraction (e.g., ⅓) of the energy generated by the imaging pixel (e.g., I22) in the second row or second sample, the collected energy may be multiplied by the fraction representing the relative area of the imaging pixel 26, 28, 60 overlapping the area represented by the super resolution pixel 80. In like manner, because a super resolution pixel 80 (e.g., S31) only includes a fraction (e.g., ⅓) of the energy generated by the imaging pixel (e.g., I32) in the third row or third sample, the collected energy may be multiplied by the fraction representing the relative area of the imaging pixel 26, 28, 60 overlapping the area represented by the super resolution pixel 80. Mathematically, the super resolution pixel energy (srpe) can be represented as the energy (ip1e) of the imaging pixel 26, 28, 60 in the first row captured in a first sample multiplied by fraction (ip1f) of the imaging pixel area in the first row overlapping the area represented by the super resolution pixel 80, the energy (ip2e) of the imaging pixel 26, 28, 60 in the second row captured in a second sample multiplied by fraction (ip2f) of the imaging pixel area in the second row overlapping the area represented by the super resolution pixel 80, and the energy (ip3e) of the imaging pixel 26, 28, 60 in the third row captured in a third sample multiplied by fraction (ip3f) of the imaging pixel area in the third row overlapping the area represented by the super resolution pixel 80 (e.g., srpe=ip1f*ip1e+ip2f*ip2e+ip3f1p3e or srpe=⅓*ip1e+⅓*ip2e+⅓*ip2e). If the fraction (ip1f) of the imaging pixel area in the first row overlapping the area represented by the super resolution pixel 80, the fraction (ip2f) of the imaging pixel area in the second row overlapping the area represented by the super resolution pixel 80, and the fraction (ip3f) of the imaging pixel area in the third row overlapping the area represented by the super resolution pixel 80 are similar or equal (ip1f=ip2f=ip3f), then the super resolution pixel energy (srpe) of each super resolution pixel can be represented by a gain factor (gf) multiplied by the energy (ip1e) of the imaging pixel 26, 28, 60 in the first row plus the energy (ip2e) of the imaging pixel 26, 28, 60 in the second row plus the energy (ip3e) of the imaging pixel 26, 28, 60 in the third row (srpe=gf*(ip1e+ip2e+ip3e)). Thus the super resolution pixel energy (srpe) of the super resolution pixels can be adjusted for the sensor unit 14a with the gain factor (gf).

The radiation energy representing the point of the object is fully represented in a super resolution pixel 80 (e.g., S33). While a neighboring super resolution pixel 80 (e.g., S32 and S34) in the shifting direction 36 contains two thirds (⅔) the radiation energy representing the point of the object as two imaging pixels 26, 28, 60 (e.g., in two of the three imaging pixel rows 32, 34, 62 in three samples) registering radiation energy representing the point of the object. But one imaging pixel 26, 28, 60 in the three imaging pixel rows 32, 34, 62 (in the three samples) does not register radiation energy representing the point of the object. A once removed super resolution pixel 80 adjacent to the neighboring super resolution pixel 80 (e.g., S31 and S35) in the shifting direction 36 contains one third (⅓) the radiation energy representing the point of the object as one imaging pixel 26, 28, 60 (e.g., in one of the three imaging pixel rows 32, 34, 62 in three samples) registering radiation energy representing the point of the object. But two imaging pixels 26, 28, 60 in the three imaging pixel rows 32, 34, 62 (in the three samples) does not register radiation energy representing the point of the object. Other non-neighboring super resolution pixel 80 (e.g., S26 and S27) in the shifting direction 36 (i.e., with at least two super resolution pixels of separation) does not contain the radiation energy representing the point of the object as none of the imaging pixels 26, 28, 60 register radiation energy representing the point of the object in the three samples (or other samples). Thus, neighboring super resolution pixel 80 and the once removed super resolution pixel 80 in the shifting direction 36 may sense or register a portion of the radiation energy representing the point of the object even when the neighboring super resolution pixel 80 and the once removed super resolution pixel 80 do not overlap with the point of the object on the sensor unit 14a.

During scanning of the object 20, the sampling frequency of the radiation detector 12 may be set such that at least one point per row of imaging pixels 26, 28, 60 is obtained. Electric signals generated by the imaging pixels 26, 28, 60 may be sampled at successive increments of movement of the sensor unit 14a in the scanning direction 24. Multiple super resolution pixels 80 (e.g., S13, S23, S33, and S43) in the scanning direction 24 representing the point of the object may be averaged together, which can also improve the resolution of the point of the object. In an example, the sensor unit 14a can use each of the super resolution pixels 80 (e.g., S13, S23, S33, and S43) in the scanning direction 24 representing the point of the object. In another example, the sensor unit 14a can use a subset of the super resolution pixels 70 (e.g., S13, S23, S33, and S43) in the scanning direction 24 representing the point of the object, such that each imaging pixel 26, 28, 60 is only represented or weighted once in super resolution pixels 80 in the scanning direction 24.

Figure 25:
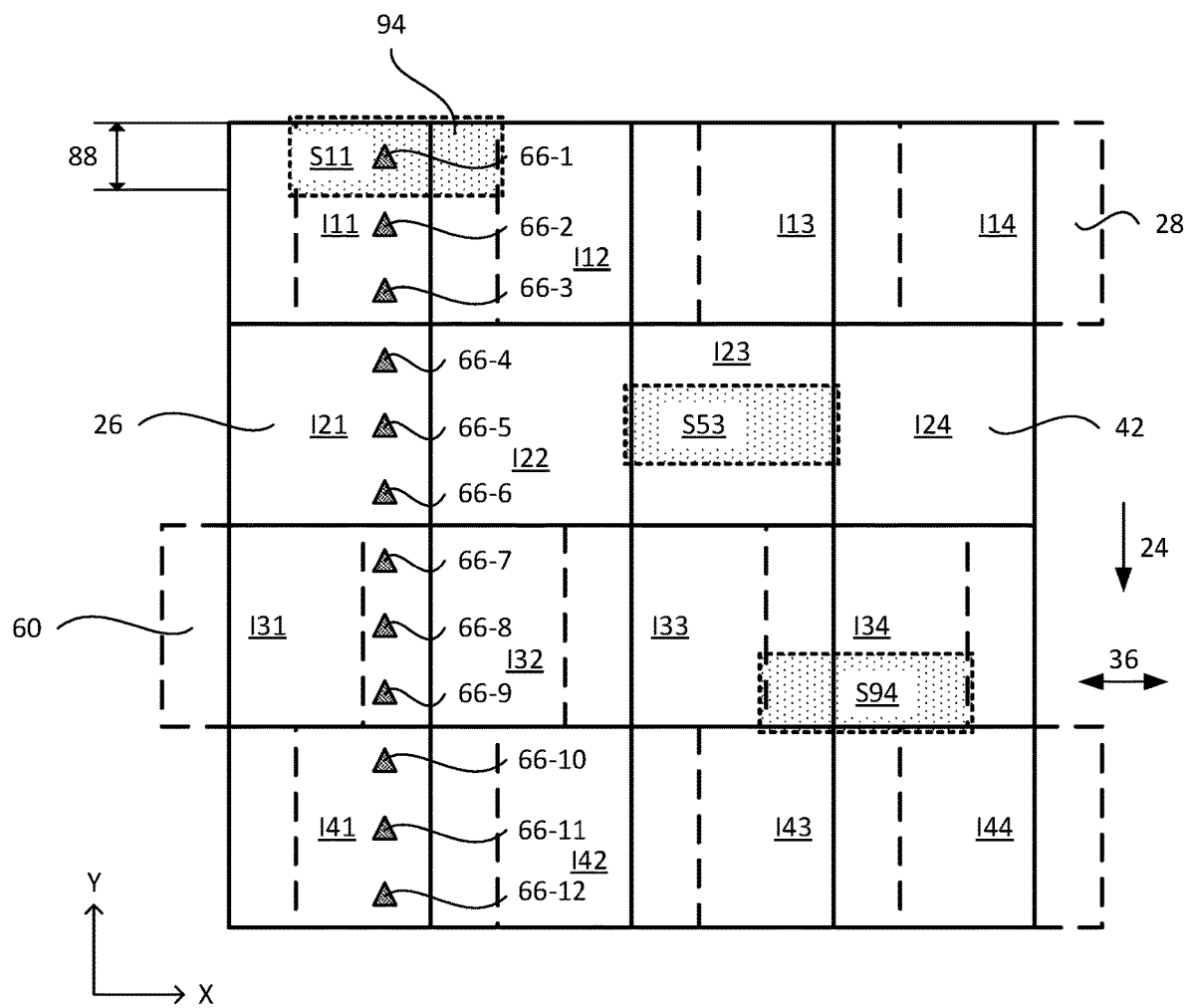
FIG. 25 schematically represents a top view of a point of an object and conceptual super resolution pixels overlaid on a conversion element over different sampling times.

FIG. 25 schematically represents a top view of a point 66 of an object 20 represented on a conversion element 22a and conceptual super resolution pixels 94 overlaid with a sampling rate of three samples per imaging pixel row 32, 34, 62 with an object moving uniformly in the scanning direction 24. In this example, information (i.e., signal and/or energy information) about the point 66 of the object 20 can be captured by the same imaging pixel 26, 28, 60 three times, so three super resolution pixels 90 occur in each imaging pixel 26, 28, 60. For example, during a first sample, information about a point 66-1 of an object 20 may be captured in a top third of the imaging pixel I11 and is represented as super resolution pixel S11. In a successive increment of movement or second sample, the information about the point 66-2 of the object 20 may be captured in a middle third of the imaging pixel I11 and is represented as super resolution pixel S21. In a successive increment of movement or third sample, the information about the point 66-3 of the object 20 may be captured in a bottom third of the imaging pixel I11 and is represented as super resolution pixel S31. The pattern continues where each imaging pixel I11, I21, I32, I41 samples the point 66-1 to 66-12 of the object 20 three times.

Prior super resolution pixel information and a difference between neighboring samples in the scanning direction 24 can be used to generate or extract information for a super resolution pixel 94 with an effective length 88 that is smaller than the imaging pixel 38. For example, the information (i.e., signal and/or energy information) for the super resolution pixel 94 can be calculated by comparing a current sample captured by the imaging pixel 26, 28, 60 with a prior or subsequent sample captured by the imaging pixel 26, 28, 60 in the scanning direction 24 plus the information for the super resolution pixels 94 in the same relative position (in the scanning direction 24) in a prior or subsequent imaging pixel 26, 28, 60 or samples. With a sampling rate of three samples per imaging pixel row 32, 34, 60 the effective length 88 as shown in FIG. 25 is approximately a third (⅓) of the imaging pixel length 38. Due to the offset between the imaging pixel 26, 28, 60 in the imaging pixel row 32, 34, 62 relative to the readout pixels 42 in the readout pixel rows 46, a resulting image (without using another approach or correction) may be skewed within a imaging pixel width 68 relative to the features of the actual object 20.

Figure 26:
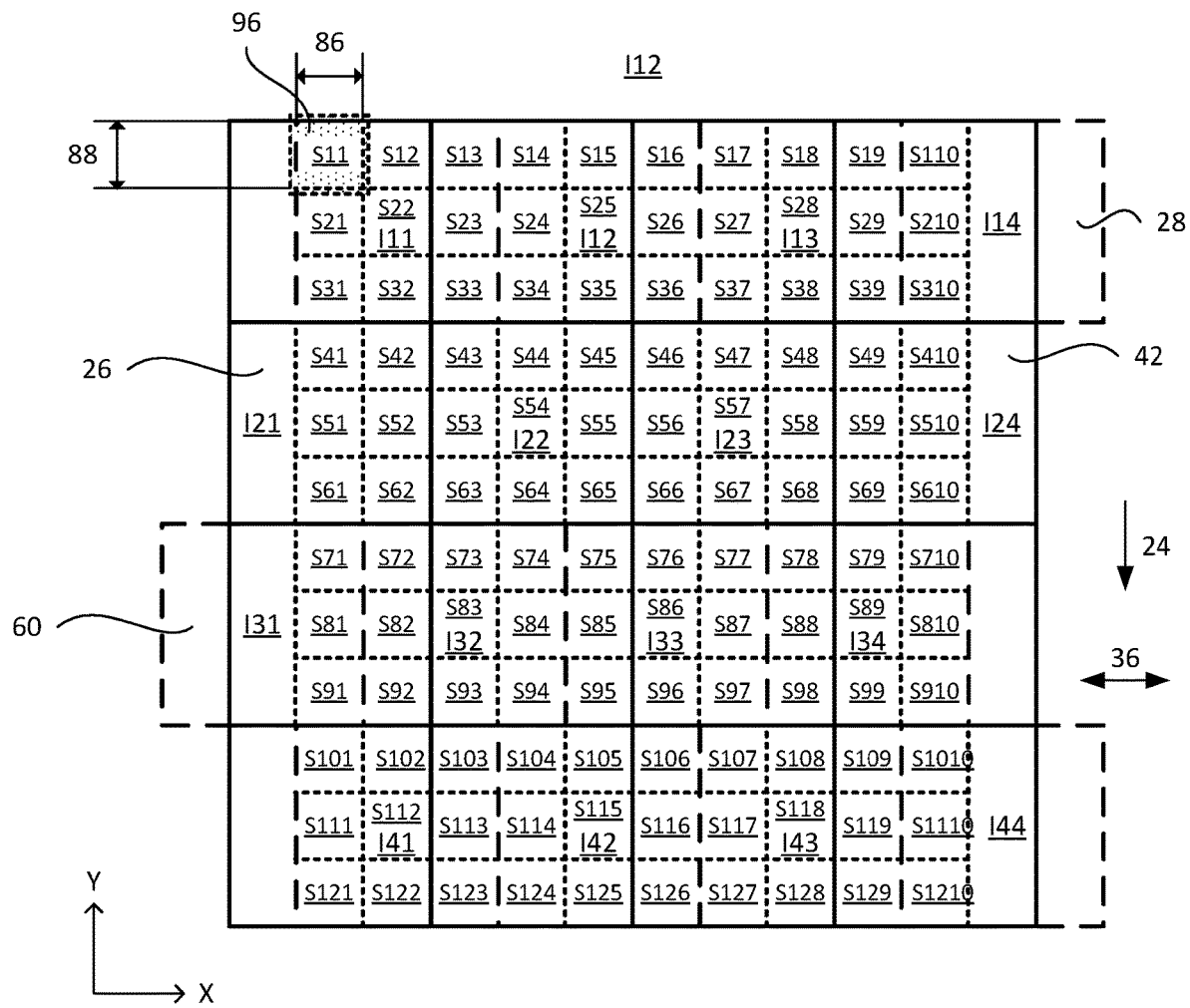
FIG. 26 schematically represents a top view of conceptual super resolution pixels overlaid on a sensor unit.

FIG. 26 schematically represents a top view of conceptual super resolution pixels overlaid on a sensor unit where each super resolution pixel 96 has an effective width 86 smaller than the imaging pixel width 68 and an effective length 88 that is smaller than the imaging pixel length 38. FIG. 26 combines the approach shown and described relative to FIGS. 23-24 to obtain a super resolution pixel 96 that has an effective width 86 smaller than the imaging pixel width 68 with the approach shown and described relative to FIG. 25 to obtain a super resolution pixel 96 having an effective length 88 that is smaller than the imaging pixel length 38. For example, one imaging pixel 26, 28, 60 (e.g., I11) can be represented by nine super resolution pixels 96 (e.g., S11, S12, S13, S21, S22, S23, S31, S32, and S33) or nine super resolution pixels 96 can be overlaid on a single imaging pixel 26, 28, 60 thus providing greater resolution than the native imaging pixel 26, 28, 60.

FIGS. 17-18 and 20 illustrate super resolution pixels 70, 92 with an effective width 76 that is approximately a half (½) of the imaging pixel width 68 using a sensor unit 14 that has one offset of the imaging pixels 26, 28 from neighboring imaging pixels 26, 28 in the scanning direction 24. FIGS. 23-24 and 26 illustrate super resolution pixel 80, 96 with an effective width 86 that is approximately a third (⅓) of the imaging pixel width 68 using a sensor unit 14a that has two offsets of the imaging pixels 26, 28 from neighboring imaging pixels 26, 28 in the scanning direction 24. In other examples, using a different number of offsets can change the effective super resolution pixel width relative of the imaging pixel width 68.

FIGS. 19-20 illustrate super resolution pixels 90, 92 with an effective length 78 that is approximately a half (½) of the imaging pixel length 38 using a sensor unit 14 that has a sampling rate of two samples per imaging pixel row 32, 34. FIGS. 25-26 illustrate super resolution pixel 94, 96 with an effective length 88 that is approximately a third (⅓) of the imaging pixel length 38 using a sensor unit 14a that has a sampling rate of three samples per imaging pixel row 32, 34, 62. In other examples, using a different sampling rate per imaging pixel row can change the effective super resolution pixel length relative of the imaging pixel length 38. Thus, the number of super resolution pixels per imaging pixel can be determined by the number of offsets of the imaging pixels from neighboring imaging pixels in the scanning direction 24 and sampling rate per imaging pixel row.

In an example, each super resolution pixel 70, 80 is configured to sense radiation energy different from a neighboring super resolution pixel 70, 80. The number of super resolution pixel 70, 80 is at least 50% or 75% greater than the number of imaging pixels 26, 26b, 28, 28b, 60 in the shifting direction 36.

In this way, a first point and a second point in an imaged object 20 may be sampled in the same first imaging pixel 26, 26b but in different second imaging pixels 28, 28b. This increases the resolution of the reconstructed image without having to tilt the sensor unit 14, 14a, 14b. The sampling may thus be performed such that a single point in an imaged object 20 is sampled at least one time for each row of imaging pixels 26, 26b, 28, 28b, 60. For example, in case the conversion element 22 comprises first rows 32 and second rows 34 according to FIG. 2, the same point in an imaged object 20 is sampled in each first row 32 and in each second row 34.

Some embodiments include a sensor unit 14, 14a, 14b for a radiation detector 12, the sensor unit 14, 14a, 14b comprising a conversion element 22, 22a, 22b comprising a plurality of imaging pixels 26, 26b, 28, 28b, 60, each imaging pixel 26, 26b, 28, 28b, 60 being configured to directly convert radiation into an electrical charge, each imaging pixel 26, 26b, 28, 28b, 60 comprising a charge collection electrode 30, 30b, and the imaging pixels 26, 26b, 28, 28b, 60 comprising first imaging pixels 26, 26b and second imaging pixels 28, 28b; and a readout substrate 40 comprising a plurality of readout pixels 42 arranged in a grid, each readout pixel 42 being connected to an associated imaging pixel 26, 26b, 28, 28b, 60 by means of an interconnection 44 at a connection position 50 on the charge collection electrode 30, 30b; wherein the second imaging pixels 28, 28b are shifted in a shifting direction 36 relative to the first imaging pixels 26, 26b; and wherein the connection positions 50 in relation to the charge collection electrodes 30, 30b are different between the first imaging pixels 26, 26b and the second imaging pixels 28, 28b.

By shifting the second imaging pixels 28, 28b in this way, the resolution of the sensor unit 14, 14a, 14b is increased. For example, two points of an imaged object 20 may travel through the same first imaging pixels 26, 26b but through different second imaging pixels 28, 28b when scanning the object 20 by means of the sensor unit 14, 14a, 14b. The sensor unit 14, 14a, 14b thereby enables higher resolution or super resolution to be obtained without having to tilt the sensor unit 14, 14a, 14b. The functioning of the sensor unit 14, 14a, 14b is thereby less complex than a tilted conventional sensor unit.

In many readout substrates 40, it is difficult and complicated to provide offsets between rows of readout pixels 42. The sensor unit 14, 14a, 14b according to the present disclosure utilizes the circumstance that for a direct conversion radiation detector 12, it does not matter where on the charge collection electrode 30, 30b the connection position 50 for the interconnection 44 is positioned. The connection position 50 can be arranged on different parts of the charge collection electrode 30, 30b to thereby enable the second imaging pixels 28, 28b to be shifted without needing to shift any readout pixels 42. The sensor unit 14, 14a, 14b allows the readout pixels 42 to be arranged in a regular grid, such as a matrix comprising readout rows 46 and readout columns 48, since the readout pixels 42 connect to connection positions 50 in relation to the associated charge collection electrodes 30, 30b that are different between the first imaging pixels 26, 26b and the second imaging pixels 28, 28b. The readout substrate 40 can therefore be of a less complex design.

The sensor unit 14, 14a, 14b further enables the same readout substrate 40 (or another readout substrate of the same design) to be used both in the sensor unit 14, 14a, 14b for high resolution imaging according to the present disclosure, and in another regular resolution sensor unit 14, 14a, 14b without shifted imaging pixels 26, 26b, 28, 28b, 60. The sensor unit 14, 14a, 14b thus has an improved modular design.

High resolution imaging typically requires high geometric magnification. Since the sensor unit 14, 14a, 14b provides an improved resolution, the requirements on a radiation source 18 can be reduced and the scanning speed can be increased. One example of requirement on a radiation source 18 is the maximum allowable kilowatts (kW) in 0.1 second.

With second imaging pixels 28, 28b shifted in a shifting direction 36 relative to the first imaging pixels 26, 26b is meant that the second imaging pixels 28, 28b are offset in the shifting direction 36 relative to the first imaging pixels 26, 26b. The connection positions 50 may for example be on a right half of the charge collection electrodes 30, 30b associated with the first imaging pixels 26, 26b, and on a left half of the charge collection electrodes 30, 30b associated with the second imaging pixels 28, 28b, or vice versa. In this case, the right and left directions are parallel with the shifting direction 36. The shifting direction 36 may be a unidirectional direction.

The connection positions 50 in relation to the charge collection electrodes 30, 30b may be the same, or substantially the same, for all first imaging pixels 26, 26b, and the connection positions 50 in relation to the charge collection electrodes 30, 30b may be the same, or substantially the same, for all second imaging pixels 28, 28b. "Substantially the same" can mean within manufacturing tolerances. For example, the connection positions 50 in relation to the charge collection electrodes 30, 30b may differ less than 5%, such as less than 2%, of a width of the first imaging pixels 26, 26b, and the connection positions 50 in relation to the charge collection electrodes 30, 30b may differ less than 5%, such as less than 2%, of a width of the second imaging pixels 28, 28b. The connection positions 50 in relation to the charge collection electrodes 30, 30b, expressed in a percentage along a width 58 of the respective charge collection electrode 30, 30b in the shifting direction 36, may differ at least 5%, such as at least 10%, between the first imaging pixels 26, 26b and the second imaging pixels 28, 28b.

Each readout pixel 42 may have a smaller area than, or the same area as, an area of an associated imaging pixel 26, 26b, 28, 28b, 60 of the plurality of imaging pixels 26, 26b, 28, 28b, 60. These areas of the readout pixels 42 and the imaging pixels 26, 26b, 28, 28b, 60 may be parallel with an imaging plane of the radiation detector 12.

The imaging pixels 26, 26b, 28, 28b, 60 may alternatively be referred to as sensor pixels or crystal pixels. The imaging pixels 26, 26b, 28, 28b, 60 may be quadrangular, such as square or rectangular, in the imaging plane. As another example, the imaging pixels 26, 26b, 28, 28b, 60 may be hexagonal in the imaging plane. The imaging pixels 26, 26b, 28, 28b, 60 may be of the same size.

The imaging pixels 26, 26b, 28, 28b, 60 may only comprise the first imaging pixels 26, 26b and the second imaging pixels 28, 28b. Alternatively, the imaging pixels 26, 26b, 28, 28b, 60 may comprise further imaging pixels 60 in addition to the first imaging pixels 26, 26b and the second imaging pixels 28, 28b.

The charge collection electrode 30, 30b may alternatively be referred to as a detector pad. The charge collection electrodes 30, 30b may have a shape corresponding to the shape of the imaging pixel 26, 26b, 28, 28b, 60, e.g. quadrangular or hexagonal. The charge collection electrodes 30, 30b may be of the same size.

Each imaging pixel 26, 26b, 28, 28b, 60 is associated with a unique readout pixel 42 among the readout pixels 42. The readout pixels 42 may alternatively be referred to as readout cells. The readout pixels 42 may be of the same size. The readout substrate 40 may comprise, or be constituted by, a readout circuit, such as an application-specific integrated circuit (ASIC).

The sensor unit 14, 14a, 14b may alternatively be referred to as a sensor module or tile. The radiation detector 12 may comprise only one sensor unit 14, 14a, 14b. Alternatively, two or more sensor units 14, 14a, 14b may be combined to provide a radiation detector 12.

The conversion element 22, 22a, 22b may comprise a continuous conversion substrate or several discrete conversion portions. In any case, a conversion element 22, 22a, 22b according to the present disclosure may comprise an element, such as a substrate, configured to produce one or more charge carriers in response to incident radiation.

In some embodiments, the shifting direction 36 is substantially perpendicular to, or perpendicular to, a scanning direction 24 of the sensor unit 14, 14a, 14b. The sensor unit 14, 14a, 14b may thus be used in a scanning radiation detector 12. The shifting direction 36 and the scanning direction 24 may be provided in the imaging plane. A shifting direction 36 substantially perpendicular to the scanning direction 24 may be angled 80° to 100°, such as 85° to 95°, relative to the scanning direction 24.

In some embodiments, the readout pixels 42 are arranged in a matrix comprising a plurality of readout rows 46 and a plurality of readout columns 48, the readout rows 46 being substantially perpendicular to, or perpendicular to, the readout columns 48 and substantially parallel with, or parallel with, the shifting direction 36. In this case, also the interconnections 44 are arranged in a corresponding matrix. Distances between adjacent interconnections 44 may be the same for several, or all, interconnections 44 of each readout row 46. Distances between adjacent interconnections 44 may be the same for several, or all, interconnections 44 of each readout column 48. As an alternative, or an addition, to a matrix comprising a plurality of readout rows 46 and a plurality of readout columns 48, the readout pixels 42 may be arranged in a hexagonal grid. Readout rows 46 substantially perpendicular to the readout columns 48 may be angled 80° to 100°, such as 85° to 95°, to the readout columns 48. Readout rows 46 substantially parallel with the shifting direction 36 may be angled less than ±10°, such as less than ±5°, relative to the shifting direction 36.

In some embodiments, the first imaging pixels 26, 26b may be arranged in first rows 32 and the second imaging pixels 28, 28b may be arranged in second rows 34. In some embodiments, each of the first rows 32 and the second rows 34 are substantially parallel with, or parallel with, the shifting direction 36. First rows 32 substantially parallel with the shifting direction 36 may be angled less than ±10°, such as less than ±5°, relative to the shifting direction 36. Each first row 32 and each second row 34 may be substantially aligned with, or aligned with, a respective readout row 46. A substantial alignment between each first row 32 and each second row 34 may include an offset of each first row 32 and each second row 34 of less than 10%, such as less than 5%, of a center-to-center distance in the scanning direction 24 between two adjacent readout pixels 42. "Substantially aligned with" can mean overlapping with sufficient space for an interconnection 44.

In some embodiments, the first rows 32 and the second rows 34 are alternatingly arranged. The imaging pixels 26, 26b, 28, 28b may only comprise the first rows 32 and the second rows 34. Alternatively, the imaging pixels 26, 26b, 28, 28b, 60 may comprise further rows of further imaging pixels 60 in addition to the first rows 32 and the second rows 34.

In some embodiments, the connection positions 50 of the first imaging pixels 26, 26b are off-center with respect to the associated charge collection electrodes 30, 30b along at least one axis or direction. In this case, the connection positions 50 of the second imaging pixels 28, 28b may be centered or differently off-centered with respect to the associated charge collection electrodes 30, 30b. In case the connection positions 50 of the second imaging pixels 28, 28b are centered with respect to the associated charge collection electrodes 30, 30b, the second imaging pixels 28, 28b may be centered with respect to the associated readout pixels 42.

In some embodiments, the connection positions 50 of the second imaging pixels 28, 28b are off-center with respect to the associated charge collection electrodes 30, 30b along at least one axis or direction. In this case, the connection positions 50 of the first imaging pixels 26, 26b may be centered or differently off-centered with respect to the associated charge collection electrodes 30, 30b. In case the connection positions 50 of the first imaging pixels 26, 26b are centered with respect to the associated charge collection electrodes 30, 30b, the first imaging pixels 26, 26b may be centered with respect to the associated readout pixels 42.

In some embodiments, the second imaging pixels 28, 28b may be shifted less than a width of the imaging pixels 26, 26b, 28, 28b, 60 from a position where the second imaging pixels 28, 28b are aligned with the first imaging pixels 26, 26b. In some embodiments, the second imaging pixels 28, 28b are be shifted half a width of the imaging pixels 26, 26b, 28, 28b, 60 from a position where the second imaging pixels 28, 28b are aligned with the first imaging pixels 26, 26b. The width may be a direction of the imaging pixels 26, 26b, 28, 28b, 60 parallel with the shifting direction 36. In a position where the second imaging pixels 28, 28b are aligned with the first imaging pixels 26, 26b, the first imaging pixels 26, 26b and second imaging pixels 28, 28b are aligned perpendicular to the shifting direction 36, e.g. parallel with the scanning direction 24.

The imaging pixels 26, 26b, 28, 28b, 60 may further comprise third imaging pixels 60. In this case, the third imaging pixels 60 may be shifted in the shifting direction 36 relative to the first imaging pixels 26, 26b differently from the second imaging pixels 28, 28b. In this case, the connection positions 50 may for example be on a right third of the charge collection electrodes 30, 30b associated with the third imaging pixels 60, on a center third of the charge collection electrodes 30, 30b associated with the first imaging pixels 26, 26b, and on a left third of the charge collection electrodes 30, 30b associated with the second imaging pixels 28, 28b.

The connection positions 50 in relation to the charge collection electrodes 30, 30b may be the same, or substantially the same, for all third imaging pixels 60. The connection positions 50 in relation to the charge collection electrodes 30, 30b, expressed in a percentage along a width 58 of the respective charge collection electrode 30, 30b in the shifting direction 36, may differ at least 5%, such as at least 10%, between the first imaging pixels 26, 26b, the second imaging pixels 28, 28b and the third imaging pixels 60.

The imaging pixels 26, 26b, 28, 28b, 60 may only comprise the first imaging pixels 26, 26b, the second imaging pixels 28, 28b and the third imaging pixels 60. Alternatively, the imaging pixels 26, 26b, 28, 28b, 60 may comprise further imaging pixels in addition to the first imaging pixels 26, 26b, the second imaging pixels 28, 28b and the third imaging pixels 60. Such further imaging pixels may form one or several further rows in addition to the first rows 32, the second rows 34 and the third rows 62.

The first imaging pixels 26, 26b may be arranged in first rows 32, the second imaging pixels 28, 28b may be arranged in second rows 34 and the third imaging pixels 60 may be arranged in third rows 62. In this case, each of the first rows 32, the second rows 34 and the third rows 62 may be substantially parallel with, or parallel with, the shifting direction 36. Each first row 32, each second row 34 and each third row 62 may be substantially aligned with, or aligned with, a respective readout row 46.

The first rows 32, the second rows 34 and the third rows 62 may be alternatingly arranged. The imaging pixels 26, 26b, 28, 28b, 60 may only comprise the first rows 32, the second rows 34 and the third rows 62. Alternatively, the imaging pixels 26, 26b, 28, 28b, 60 may comprise one or several further rows of further imaging pixels 26, 26b, 28, 28b, 60 in addition to the first rows 32, the second rows 34 and the third rows 62. In this case, each row of imaging pixels 26, 26b, 28, 28b, 60, except first rows 32 of imaging pixels 26, 26b, may have a unique offset in the shifting direction 36 with respect to the first rows 32 of imaging pixels 26, 26b.

The connection positions 50 of the third imaging pixels 60 may be off-center with respect to the associated charge collection electrodes 30, 30b. In this case, the connection positions 50 of the first imaging pixels 26, 26b may be centered or differently off-centered with respect to the associated charge collection electrodes 30, 30b and the connection positions 50 of the second imaging pixels 28, 28b may be centered or differently off-centered with respect to the associated charge collection electrodes 30, 30b.

The third imaging pixels 60 may be shifted less than a width of the imaging pixels 26, 26b, 28, 28b, 60 from a position where the third imaging pixels 60 are aligned with the first imaging pixels 26, 26b. For example, the second imaging pixels 28, 28b may be shifted a third of a width of the imaging pixels 26, 26b, 28, 28b, 60 to the right from a position where the second imaging pixels 28, 28b are aligned with the first imaging pixels 26, 26b, and the third imaging pixels 60 may be shifted a third of a width of the imaging pixels 26, 26b, 28, 28b, 60 to the left from the position where the third imaging pixels 60 are aligned with the first imaging pixels 26, 26b.

In some embodiments, each readout pixel 42 comprises readout pixel electronics 56 with at least one electronic component specific for an associated readout pixel 42. In some embodiments, the at least one electronic component comprises an amplifier, a comparator and/or a counter for counting photon pulses.

In some embodiments, each interconnection 44 comprises a solder bump, e.g. by direct bonding. Each readout pixel 42 may comprise a readout contact pad to which the solder bump can be deposited. An interconnection 44 according to the present disclosure may however alternatively comprise any type of connection member for creating electrical contact, e.g. between an imaging pixel 26, 26b, 28, 28b, 60 and a readout pixel 42.

In some embodiments, the conversion element 22, 22a, 22b comprises a semiconductor substrate, such as a cadmium telluride (CdTe) or a cadmium zinc telluride (CdZnTe or CZT) substrate.

In some embodiments, each imaging pixel 26, 26b, 28, 28b, 60 is configured to directly convert ionizing radiation into an electrical charge.

Some embodiments include a radiation detector 12 comprising at least one sensor unit 14, 14a, 14b according to the present disclosure. Throughout the present disclosure, the radiation detector 12 may be constituted by a direct conversion radiation detector 12. The radiation detector 12 may alternatively be referred to as a radiation imaging device. The radiation detector 12 may be a scanning radiation detector 12.

Some embodiments include an imaging apparatus 10 comprising at least one sensor unit 14, 14a, 14b according to the present disclosure or at least one radiation detector 12 according to the present disclosure. The imaging apparatus 10 may further comprise a control system 16 and a radiation source 18.

Some embodiments include a method of manufacturing a sensor unit 14, 14a, 14b for a radiation detector 12, the method comprising providing a conversion element 22, 22a, 22b comprising a plurality of imaging pixels 26, 26b, 28, 28b, 60, each imaging pixel 26, 26b, 28, 28b, 60 being configured to directly convert radiation into an electrical charge, each imaging pixel 26, 26b, 28, 28b, 60 comprising a charge collection electrode 30, 30b, and the imaging pixels 26, 26b, 28, 28b, 60 comprising first imaging pixels 26, 26b and second imaging pixels 28, 28b; providing a readout substrate 40 comprising a plurality of readout pixels 42 arranged in a grid; and connecting each readout pixel 42 to an associated imaging pixel 26, 26b, 28, 28b, 60 by means of an interconnection 44 at a connection position 50 on the charge collection electrode 30, 30b; wherein the second imaging pixels 28, 28b are shifted in a shifting direction 36 relative to the first imaging pixels 26, 26b; and wherein the connection positions 50 in relation to the charge collection electrodes 30, 30b are different between the first imaging pixels 26, 26b and the second imaging pixels 28, 28b. The sensor unit 14, 14a, 14b manufactured by the method may be of any type according to the present disclosure.

In some embodiments, the connection of the charge collection electrode 30, 30b to the readout substrate 40 may use solder bump bonding, direct bonding, or flip-chip bonding.

Some embodiments include a sensor unit 14, 14a, 14b manufactured by any method according to the present disclosure or a sensor unit 14, 14a, 14b resulting from any method according to the present disclosure.

Some embodiments include a method of using a sensor unit 14, 14a, 14b for a radiation detector 12, the method comprising providing S4 a sensor unit 14, 14a, 14b comprising a conversion element 22, 22a, 22b comprising a plurality of imaging pixels 26, 26b, 28, 28b, 60, each imaging pixel 26, 26b, 28, 28b, 60 being configured to directly convert radiation into an electrical charge, each imaging pixel 26, 26b, 28, 28b, 60 comprising a charge collection electrode 30, 30b, and the imaging pixels 26, 26b, 28, 28b, 60 comprising first imaging pixels 26, 26b and second imaging pixels 28, 28b; and a readout substrate 40 comprising a plurality of readout pixels 42 arranged in a grid, each readout pixel 42 being connected to an associated imaging pixel 26, 26b, 28, 28b, 60 by means of an interconnection 44 at a connection position 50 on the charge collection electrode 30, 30b; wherein the second imaging pixels 28, 28b are shifted in a shifting direction 36 relative to the first imaging pixels 26, 26b; and wherein the connection positions 50 in relation to the charge collection electrodes 30, 30b are different between the first imaging pixels 26, 26b and the second imaging pixels 28, 28b. The method further comprises moving S5 the sensor unit 14, 14a, 14b in a scanning direction 24 substantially perpendicular to the shifting direction 36; generating S6 electric signals responsive to radiation onto the imaging pixels 26, 26b, 28, 28b, 60; and sampling S7 the electric signals at successive increments of movement of the sensor unit 14, 14a, 14b in the scanning direction 24 equal to or less than a length 38 of each imaging pixel 26, 26b, 28, 28b, 60 in the scanning direction 24.

The method may further comprise sampling the electric signals at successive increments of movement of the sensor unit 14, 14a, 14b in the scanning direction 24 such that at least one point per row of imaging pixels 26, 26b, 28, 28b, 60 is obtained for a single point in an imaged object 20. When the rows of imaging pixels 26, 26b, 28, 28b are perpendicular to the scanning direction 24, the electric signals are easier to process in comparison with a sensor unit tilted in an imaging plane.

In some embodiments, the method further comprises generating an image from super resolution pixels 70, 80, wherein each super resolution pixel 70, 80 is derived from at least two successive imaging pixels 26, 26b, 28, 28b, 60 in the scanning direction 24 with a super resolution pixel width 76, 86 that is less than 75% of an imaging pixel width 68.

In some embodiments, each super resolution pixel 70, 80 is configured to generate radiation energy values different from a neighboring super resolution pixel 70, 80 and the number of super resolution pixel 70, 80 is at least 50% greater than the number of imaging pixels 26, 26b, 28, 28b, 60 in the shifting direction 36.

Some embodiments include a sensor unit for a radiation detector, the sensor unit comprising: a plurality of means for directly converting radiation into an electrical charge divided into a plurality of first means for directly converting radiation into an electrical charge and a plurality of second means for directly converting radiation into an electrical charge, each means for directly converting radiation into an electrical charge including means for collecting charge; and a plurality of means for reading out an electrical signal from an associated one of the means for directly converting radiation into an electrical charge; and a plurality of means for interconnecting each of the means for reading out an electrical signal to a connection position of the means for collecting charge of the associated one of the means for directly converting radiation into an electrical charge; wherein the second means for directly converting radiation into an electrical charge are shifted in a shifting direction relative to the first means for directly converting radiation into an electrical charge; and wherein the connection positions of the means for collecting charge are different between the first means for directly converting radiation into an electrical charge and the second means for directly converting radiation into an electrical charge.

Examples of the means for directly converting radiation into an electrical charge include the imaging pixels 26, 26b, 28, 28b, 60. Examples of the first means for directly converting radiation into an electrical charge include first imaging pixels 26, 26b. Examples of the second means for directly converting radiation into an electrical charge include second imaging pixels 28, 28b. Examples of the means for collecting charge include charge collection electrodes 30, 30b. Examples of the means for interconnecting include interconnection 44 and connection positions 50. Examples of means for reading out an electrical signal include readout pixels 42.

In some embodiments the sensor unit further comprises means for generating an image from at least two successive means for directly converting radiation into an electrical charge in the scanning direction with a width of the means for generating an image that is less than 75% of a width of means for directly converting radiation into an electrical charge width. Examples of the means for generating an image include super resolution pixels 70, 80.

In some embodiments the sensor unit further comprises means for generating radiation energy values different from a neighboring means for generating an image and the number of means for generating an image is at least 50% greater than the number of the means for directly converting radiation into an electrical charge in the shifting direction. Examples of the means for generating radiation energy values different from a neighboring means for generating an image include super resolution pixels 70, 80.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the spirit and scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 4 can depend from either of claims 1 and 3, with these separate dependencies yielding two distinct embodiments; claim 5 can depend from any one of claim 1, 3, or 4, with these separate dependencies yielding three distinct embodiments; claim 6 can depend from any one of claim 1, 3, 4, or 5, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112(f). Embodiments of the invention in which an exclusive property or privilege is claimed are defined as follows.

The invention claimed is:

1. A sensor unit for a radiation detector, the sensor unit comprising:
a conversion element comprising a plurality of imaging pixels, each imaging pixel being configured to directly convert radiation into an electrical charge, each imaging pixel comprising a charge collection electrode, and the imaging pixels comprising first imaging pixels and second imaging pixels; and
a readout substrate comprising a plurality of readout pixels arranged in a grid, each readout pixel being connected to an associated imaging pixel by means of an interconnection at a connection position on the charge collection electrode;
wherein the second imaging pixels are shifted in a shifting direction relative to the first imaging pixels; and
wherein the connection positions in relation to the charge collection electrodes are different between the first imaging pixels and the second imaging pixels.

2. The sensor unit of claim 1, wherein:
the shifting direction is substantially perpendicular to a scanning direction of the sensor unit.

3. The sensor unit of claim 1, wherein:
the readout pixels are arranged in a matrix comprising a plurality of readout rows and a plurality of readout columns, the readout rows being substantially perpendicular to the readout columns and substantially parallel with the shifting direction.

4. The sensor unit of claim 1, wherein:
the first imaging pixels are arranged in first rows and the second imaging pixels are arranged in second rows, each of the first rows and the second rows being substantially parallel with the shifting direction.

5. The sensor unit of claim 4, wherein:
each first row and each second row is substantially aligned with a respective readout row.

6. The sensor unit of claim 5, wherein:
the first rows and the second rows are alternatingly arranged.

7. The sensor unit of claim 1, wherein:
the connection positions of the first imaging pixels are off-center with respect to the associated charge collection electrodes.

8. The sensor unit of claim 1, wherein:
the connection positions of the second imaging pixels are off-center with respect to the associated charge collection electrodes.

9. The sensor unit of claim 1, wherein:
the second imaging pixels are shifted less than a width of the imaging pixels from a position where the second imaging pixels are aligned with the first imaging pixels.

10. The sensor unit of claim 1, wherein:
the second imaging pixels are shifted half a width of the imaging pixels from a position where the second imaging pixels are aligned with the first imaging pixels.

11. The sensor unit of claim 1, wherein:
each readout pixel comprises readout pixel electronics with at least one electronic component specific for an associated readout pixel.

12. The sensor unit of claim 11, wherein:
the at least one electronic component comprises an amplifier, a comparator and/or a counter for counting photon pulses.

13. The sensor unit of claim 1, wherein:
each interconnection comprises a solder bump.

14. The sensor unit of claim 1, wherein:
the conversion element comprises a semiconductor substrate, such as a cadmium telluride (CdTe) or a cadmium zinc telluride (CdZnTe or CZT) substrate.

15. The sensor unit of claim 1, wherein:
each imaging pixel is configured to directly convert ionizing radiation into an electrical charge.

16. A method of using a sensor unit for a radiation detector, the method comprising:
providing a sensor unit comprising:
a conversion element comprising a plurality of imaging pixels, each imaging pixel being configured to directly convert radiation into an electrical charge, each imaging pixel comprising a charge collection electrode, and the imaging pixels comprising first imaging pixels and second imaging pixels; and
a readout substrate comprising a plurality of readout pixels arranged in a grid, each readout pixel being connected to an associated imaging pixel by means of an interconnection at a connection position on the charge collection electrode;
wherein the second imaging pixels are shifted in a shifting direction relative to the first imaging pixels; and
wherein the connection positions in relation to the charge collection electrodes are different between the first imaging pixels and the second imaging pixels;
moving the sensor unit in a scanning direction substantially perpendicular to the shifting direction;
generating electric signals responsive to radiation onto the imaging pixels; and
sampling the electric signals at successive increments of movement of the sensor unit in the scanning direction equal to or less than a length of each imaging pixel in the scanning direction.

17. The method according to claim 16, further comprising:
generating an image from super resolution pixels, wherein each super resolution pixel is derived from at least two successive imaging pixels in the scanning direction with a super resolution pixel width that is less than 75% of an imaging pixel width.

18. The method according to claim 17, wherein each super resolution pixel is configured to generate radiation energy values different from a neighboring super resolution pixel and the number of super resolution pixel is at least 50% greater than the number of imaging pixels in the shifting direction.

19. A sensor unit for a radiation detector, the sensor unit comprising:
a plurality of means for directly converting radiation into an electrical charge divided into a plurality of first means for directly converting radiation into an electrical charge and a plurality of second means for directly converting radiation into an electrical charge, each means for directly converting radiation into an electrical charge including means for collecting charge;
a plurality of means for reading out an electrical signal from an associated one of the means for directly converting radiation into an electrical charge; and
a plurality of means for interconnecting each of the means for reading out an electrical signal to a connection position of the means for collecting charge of the associated one of the means for directly converting radiation into an electrical charge;
wherein the second means for directly converting radiation into an electrical charge are shifted in a shifting direction relative to the first means for directly converting radiation into an electrical charge; and
wherein the connection positions of the means for collecting charge are different between the first means for directly converting radiation into an electrical charge and the second means for directly converting radiation into an electrical charge.

20. The sensor unit of claim 19, further comprising:
means for generating an image from at least two successive means for directly converting radiation into an electrical charge in the scanning direction with a width of the means for generating an image that is less than 75% of a width of means for directly converting radiation into an electrical charge width.

21. The sensor unit of claim 20, further comprising:
means for generating radiation energy values different from a neighboring means for generating an image and the number of means for generating an image is at least 50% greater than the number of the means for directly converting radiation into an electrical charge in the shifting direction.

* * * * *

UNITED STATES PATENT AND TRADEMARK OFFICE
CERTIFICATE OF CORRECTION

| | | |
|---|---|---|
| PATENT NO. | : 11,536,860 B2 | Page 1 of 1 |
| APPLICATION NO. | : 17/359408 | |
| DATED | : December 27, 2022 | |
| INVENTOR(S) | : Christer Ullberg | |

It is certified that error appears in the above-identified patent and that said Letters Patent is hereby corrected as shown below:

On the Title Page

Please insert below item (22):
--(30) Foreign Application Priority Data
June 26, 2020 (SE) ....................2050777-8--

Signed and Sealed this
Twenty-seventh Day of August, 2024

*Katherine Kelly Vidal*

Katherine Kelly Vidal
*Director of the United States Patent and Trademark Office*